(12) United States Patent
Wakai

(10) Patent No.: US 9,192,347 B2
(45) Date of Patent: Nov. 24, 2015

(54) MEDICAL IMAGE PROCESSING SYSTEM APPLYING DIFFERENT FILTERING TO COLLATERAL CIRCULATION AND ISCHEMIC BLOOD VESSELS

(71) Applicants:KABUSHIKI KAISHA TOSHIBA, Minato-ku (JP); TOSHIBA MEDICAL SYSTEMS CORPORATION, Otawara-Shi (JP)

(72) Inventor: Satoshi Wakai, Nasushiobara (JP)

(73) Assignees: KABUSHIKI KAISHA TOSHIBA, Minato-Ku (JP); TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 44 days.

(21) Appl. No.: 13/908,225

(22) Filed: Jun. 3, 2013

(65) Prior Publication Data

US 2013/0259336 A1 Oct. 3, 2013

Related U.S. Application Data

(63) Continuation of application No. PCT/JP2012/075684, filed on Oct. 3, 2012.

(30) Foreign Application Priority Data

Oct. 17, 2011 (JP) .................................. 2011-228076

(51) Int. Cl.
*G06K 9/00* (2006.01)
*A61B 6/00* (2006.01)
(Continued)

(52) U.S. Cl.
CPC ................. *A61B 6/504* (2013.01); *A61B 6/501* (2013.01); *A61B 6/5217* (2013.01);
(Continued)

(58) Field of Classification Search
None
See application file for complete search history.

(56) References Cited

U.S. PATENT DOCUMENTS

| 5,602,891 | A | 2/1997 | Pearlman |
| 2003/0181809 | A1 | 9/2003 | Hall et al. |

(Continued)

FOREIGN PATENT DOCUMENTS

| JP | 5-56974 | 3/1993 |
| JP | 2002-515772 | 5/2002 |

(Continued)

OTHER PUBLICATIONS

Higashino et al. Image Fusion of Coronary Tree and Regional Cardiac Function Image Using Multislice Computed Tomography, 2006, Circulation Journal, 70: 105-109.*

(Continued)

*Primary Examiner* — Jason Heidemann
(74) *Attorney, Agent, or Firm* — Oblon, McClelland, Maier & Neustadt, L.L.P.

(57) ABSTRACT

A medical image processing system includes an angiographic image acquisition unit, a volume data generation unit, a vessel extraction unit, a sorting unit, and an image synthesis unit. The angiographic image acquisition unit acquires an angiographic image on a region including a blood vessel. The volume data generation unit three-dimensionally reconstructs the angiographic image to generate volume data. The vessel extraction unit extracts blood vessels on the basis of the volume data. The sorting unit sorts collateral circulations and ischemic blood vessels on the basis of the blood vessels. The image synthesis unit applies different image processes to the collateral circulations and the ischemic blood vessels, and generates a synthesized image.

13 Claims, 28 Drawing Sheets

(51) Int. Cl.
*G06F 19/00* (2011.01)
*G06T 5/50* (2006.01)

(52) U.S. Cl.
CPC ............... *G06F 19/321* (2013.01); *G06T 5/50* (2013.01); *A61B 6/4225* (2013.01); *A61B 6/466* (2013.01); *A61B 6/481* (2013.01); *A61B 6/487* (2013.01); *A61B 6/5229* (2013.01); *G06T 2207/10016* (2013.01); *G06T 2207/30101* (2013.01)

(56) References Cited

U.S. PATENT DOCUMENTS

| | | | |
|---|---|---|---|
| 2005/0015006 A1* | 1/2005 | Mitschke et al. | 600/431 |
| 2005/0046644 A1* | 3/2005 | Ohishi | 345/643 |
| 2008/0081980 A1* | 4/2008 | Maschke et al. | 600/407 |
| 2009/0010519 A1* | 1/2009 | Wakai et al. | 382/131 |
| 2009/0129649 A1* | 5/2009 | Djeridane | 382/131 |
| 2009/0328239 A1* | 12/2009 | Brauner et al. | 800/3 |
| 2010/0002839 A1* | 1/2010 | Yokota et al. | 378/98.12 |
| 2010/0014727 A1* | 1/2010 | Hu | 382/128 |
| 2011/0103657 A1* | 5/2011 | Kang et al. | 382/128 |
| 2011/0103666 A1 | 5/2011 | Ohishi | |
| 2012/0226141 A1* | 9/2012 | Shinoda et al. | 600/419 |

FOREIGN PATENT DOCUMENTS

| | | |
|---|---|---|
| JP | 2003-290192 | 10/2003 |
| JP | 2006-198060 | 8/2006 |
| JP | 2008-206556 | 9/2008 |
| JP | 2009-125582 | 6/2009 |
| JP | 2011-115562 | 6/2011 |
| WO | 97/17673 | 5/1997 |
| WO | 2007/026598 | 3/2007 |

OTHER PUBLICATIONS

International Search Report issued on Nov. 6, 2012 for PCT/JP2012/075684 filed on Oct. 3, 2012 with English Translation.
International Written Opinion issued on Nov. 6, 2012 for PCT/JP2012/075684 filed on Oct. 3, 2012.
International Preliminary Report on Patentability and Written Opinion issued Apr. 22, 2014 in PCT/JP2012/075684 (submitting English translation only).
Office Action issued Aug. 18, 2015 in Japanese Patent Application No. 2011-228076.

* cited by examiner

MEDICAL IMAGE PROCESSING SYSTEM APPLYING DIFFERENT FILTERING TO COLLATERAL CIRCULATION AND ISCHEMIC BLOOD VESSELS

CROSS-REFERENCE TO RELATED APPLICATION

This application is a Continuation Application of No. PCT/JP2012/75684, filed on Oct. 3, 2012, and the PCT application is based upon and claims the benefit of priority from Japanese Patent Application No. 2011-228076, filed on Oct. 17, 2011, the entire contents of which are incorporated herein by reference.

FIELD

A present embodiment as one aspect of the present invention relates to a medical image processing system which generates images and performs image data processing.

BACKGROUND

For imaging blood vessels with an enhanced contrast with a contrast agent, a contrast-enhanced X-ray image diagnostic apparatus is known. The apparatus includes, for example, an X-ray tube and an FPD (flat panel detector) or an I.I. (image intensifier), which are each provided on both ends of a generally C-shaped support (C-arm), and an image processing section. The contrast-enhanced X-ray image diagnostic apparatus is also generally referred to as an angiographic apparatus, which can be used by doctors for diagnosis and treatment (medical examination) such as catheter insertion to a patient as an object and for X-ray photography.

Generally, for observation of collateral circulations and their peripheral blood vessels, there is a medical image pickup technology with X-ray image diagnostic apparatuses, X-ray CT (computed tomography) apparatuses, and MRI (magnetic resonance imaging) apparatuses.

As a conventional technology, there is a technology of obtaining images that show various structures of interested organizations such as blood vessels in an easily understandable way.

In the conventional technology, collateral circulations, which are extracted based on angiographic images (including non-contrast enhanced MRA images obtained without a contrast agent) collected by medical diagnostic imaging apparatuses such as X-ray CT apparatuses, MRI apparatuses and contrast-enhanced X-ray image diagnostic apparatuses, are locally concentrated, and therefore, they are extracted on images as clouds typically seen in the case of moyamoya disease (occlusive disease in circle of Willis). Under these circumstances, the collateral circulations have been an obstacle in observing peripheral vessel structures with use of angiographic images. Moreover, blood vessels that position downstream from a collateral circulation are often shown as minute streams on images as their blood flow rate is low. Accordingly, due to the presence of the collateral circulation, it has been difficult to grasp peripheral vessel structures.

BRIEF DESCRIPTION OF THE DRAWINGS

In accompanying drawings.

DETAILED DESCRIPTION

A medical image processing system according to the present embodiment will be described with reference to accompanying drawings.

To solve the above-described problems, the present embodiments provide the medical image processing system including: an angiographic image acquisition unit configured to acquire an angiographic image on a region including a blood vessel; a volume data generation unit configured to three-dimensionally reconstruct the angiographic image to generate volume data; a vessel extraction unit configured to extract blood vessels on the basis of the volume data; a sorting unit configured to sort collateral circulations and ischemic blood vessels on the basis of the blood vessels; and an image synthesis unit configured to apply different image processes to the collateral circulations and the ischemic blood vessels, and to generate a synthesized image.

According to the medical image processing system in the present embodiment, images with visible vessel structures can be generated.

First Embodiment

Figure 1:
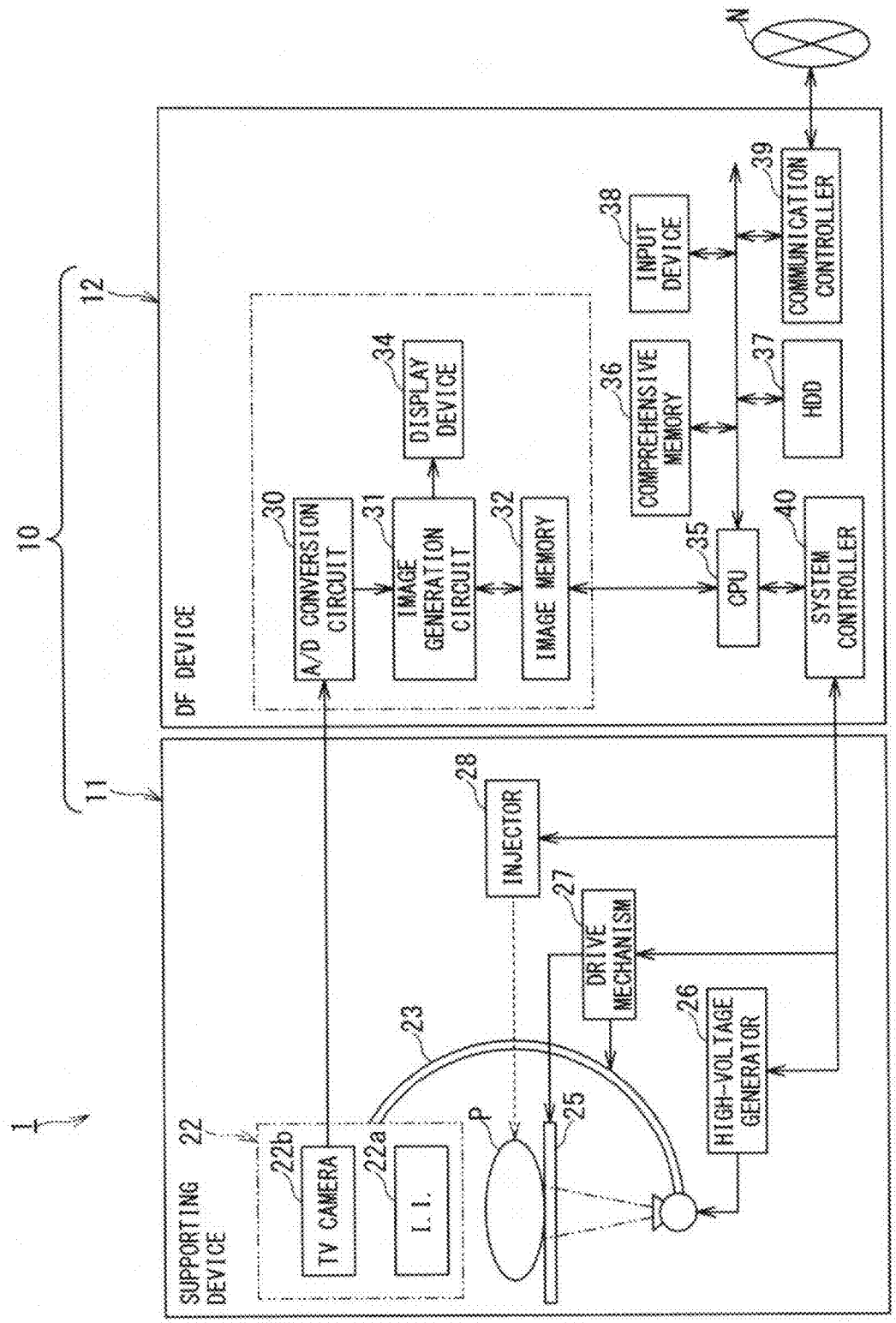
FIG. 1 is a schematic diagram showing an example of a structure of a medical image processing system according to a first embodiment.

FIG. 1 is a schematic diagram showing an example of a structure of a medical image processing system according to a first embodiment.

FIG. 1 shows a medical image processing system 1 according to the first embodiment. The medical image processing system 1 includes an angiographic apparatus 10 as an X-ray image diagnostic apparatus. The angiographic apparatus 10 is mainly constituted of a supporting device 11 and a DF (digital fluorography) device 12.

The supporting device 11 includes an X-ray tube 21, an X-ray detector 22, a C-arm 23, a table-top (catheter table) 25, a high-voltage generator 26, a drive mechanism 27, and an automatic contrast agent injector (injector) 28. Although a description will be given of the supporting device 11 of an under-tube-type in which the X-ray tube 21 is positioned below the table-top 25, the supporting device 11 may be of an over-tube-type in which the X-ray tube 21 is positioned above the table-top 25. On an X-ray emission side of the X-ray tube 21, there may be provided an X-ray irradiation field diaphragm that is composed of a plurality of lead blades, and a compensating filer that is formed of silicon rubber or the like for attenuating a specified amount of an irradiated X-ray so as to prevent halation.

The X-ray tube 21, which is provided in one end of the C-arm 23, receives high voltage power from the high-voltage generator 26 and irradiates an object (patient) P with an X-ray in response to conditions of the high voltage power.

The X-ray detector 22 is provided in another end of the C-arm 23, which is an emission side of the X-ray tube 21, to detect an X-ray which has transmitted through the patient P. The X-ray detector 22 is an I.I. (image intensifier)-TV system, and mainly includes an I.I. 22a and a TV camera 22b. The X-ray detector 22 may also be embodied by an FPD (flat panel detector).

The I.I. 22a converts the X-ray that has transmitted through the patient P, into visible light, and further multiplies luminance in process of light-electron-light conversion to form highly sensitive projection data. The TV camera 22b converts optical projection data into electrical signals with use of a CCD (charge coupled device) image sensor.

The C-arm 23 supports the X-ray tube 21 at one end and the X-ray detector 22 at the other end so that the X-ray tube 21 and the X-ray detector 22 are placed face to face about the patient P. A moving amount, movement timing, and a moving speed of the C-arm 23 are controlled by the drive mechanism 27.

The table-top 25 is used to lay the patient P thereon.

The high-voltage generator 26 generates high voltage power to the X-ray tube 21 under a control of the DF device 12.

Under the control of the DF device 12, the drive mechanism 27 moves the C-arm 23 so as to draw an circular arc (in an LAO (left anterior oblique view) direction and in an RAO (right anterior oblique view) direction) or rotates the C-arm 23 (in a CRA (cranial view) direction and a CAU (caudal view) direction).

The drive mechanism 27 also moves the C-arm 23 in parallel with a longitudinal direction of the table-top 25 that holds the patient P or stands and reclines the C-arm 23 integrally with the table-top 25 under the control of the DF device 12. The drive mechanism 27 further moves the C-arm 23 straight in the longitudinal direction of the table-top 25 that holds the patient P under the control of the DF device 12, so that the X-ray tube 21 and the X-ray detector 22 are moved in the longitudinal direction of the table-top 25 that holds the patient P for imaging. In addition, the drive mechanism 27 moves the table-top 25 in a vertical direction, a horizontal direction, and a longitudinal direction under the control of the DF device 12.

The injector 28 is an apparatus for injecting a contrast agent into a contrast agent catheter (not shown) that has inserted into an involved part of the patient P under the control of the DF device 12.

The DF device 12, which is structured by a computer as a base, can mutually communicate with a network N such as a hospital-based LAN (local area network). The DF device 12 is mainly constituted of hardware devices such as an A/D (analog to digital) conversion circuit 30, an image generation circuit 31, an image memory 32, a display device 34, a CPU (central processing unit) 35 as a processor, a comprehensive memory 36, an HDD (hard disc drive) 37, an input device 38, a communication controller 39, and a system controller 40. The CPU 35 is mutually connected with respective hardware components that constitute the DF device 12 via a bus as a common signal transmission line. The DF device 12 may include a recording medium drive (not shown).

The A/D conversion circuit 30 converts time-series analog signals (video signals) outputted from the X-ray detector 22 into digital signals.

Under a control of the CPU 35, the image generation circuit 31 applies logarithmic conversion processing (LOG processing) to digital signals of projection data outputted from the A/D conversion circuit 30, applies addition processing thereto, where necessary, to generate frame-based image data, and stores the image data in the image memory 32. The image generation circuit 31 also applies image processing to the frame-based image data, and stores the image data after image processing in the image memory 32. Examples of the image processing include magnification, gradation, spatial filtering of the image data, tracing of minimum-value/maximum-value of sequentially stored image data, and addition processing for noise removal. The image data generated by the image generation circuit 31 is outputted to the CPU 35 and is stored in a storage device such as the image memory 32.

The image memory 32 stores the image data outputted from the image generation circuit 31 under the control of the CPU 35.

The display device 34 includes an image memory for display such as a VRAM (video random access memory device, not shown), a D/A (digital to analog) converter, and a display circuit. Under the control of the CPU 35, data such as image data to be displayed is expanded in the VRAM, by which the image data is displayed on the display device 34. Synthesized images outputted from the CPU 35 are displayed as static images or reproduced moving images.

The CPU 35 is a controller having a packaged integrated circuit (LSI) structure in which an electronic circuit made of semiconductors has a plurality of terminals. Once a command is inputted by operation of the input device 38 or the like by an operator such as a doctor and an engineer, the CPU 35 executes a program stored in the comprehensive memory 36. Alternatively, the CPU 35 loads to the comprehensive memory 36 a program stored in the HDD 37, a program transferred from the network N, received in the communication controller 39 and installed in the HDD 37, or a program read from a recording medium mounted on a recording media drive (not shown) and installed in the HDD 37. The CPU 35 then executes the loaded program.

The comprehensive memory 36 includes ROM (read only memory), RAM (random access memory) or the like. The comprehensive memory 36 is a storage device that stores an IPL (initial program loading), a BIOS (BASIC input/output system) and data, and is also used for temporary storage of work memory and data of the CPU 35.

The HDD 37 is a storage device structured to unremovably incorporate a metal disk in which magnetic substances are applied or vapor-deposited thereto. The HDD 37 stores programs (including application programs and OS (operating system)) installed in the DF device 12 and data. It is also possible to provide GUIs (graphical user interfaces) which allow for heavy use of graphics to display information to users and allow for basic operations to be performed by the input device 38 to OS.

The input device 38 includes such components as a keyboard and a mouse operable by an operator. Input signals in response to the operation are sent to the CPU 35. The input device 38 is mainly constituted of a main console and a system console.

The communication controller 39 performs communication control in conformity to each protocol. The communication controller 39 has a function allowing connection to the network N. As a consequence, the angiographic apparatus 10 can be connected to the network N through the communication controller 39.

The system controller 40 includes a not shown CPU and memory devices. The system controller 40 controls operation of the high voltage generator 26, the drive mechanism 27 and the injector 28 in the supporting device 11 according to instructions from the CPU 35.

Figure 2:
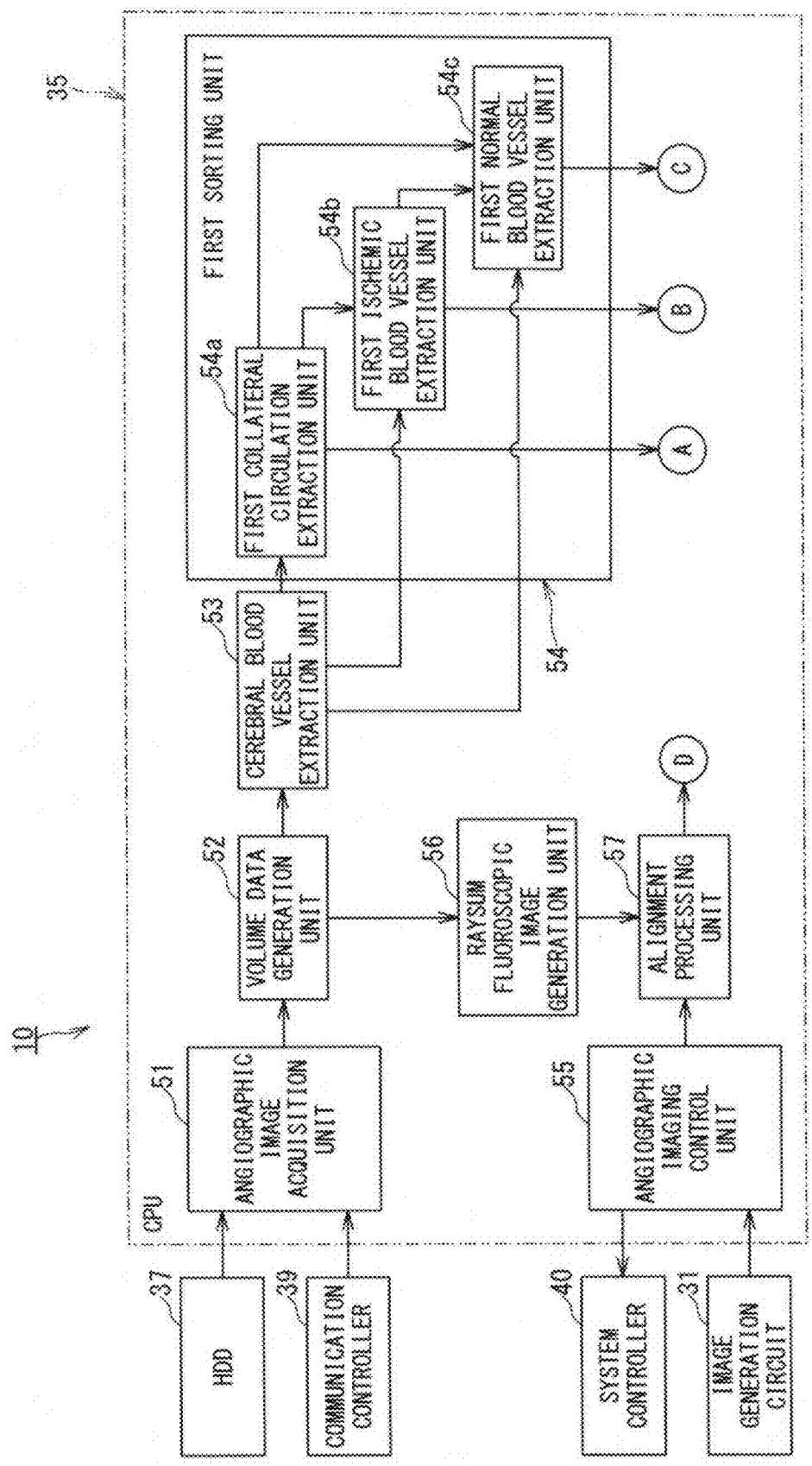
FIG. 2 is a block diagram showing functions of an angiographic apparatus in the medical image processing system according to the first embodiment.
Figure 3:
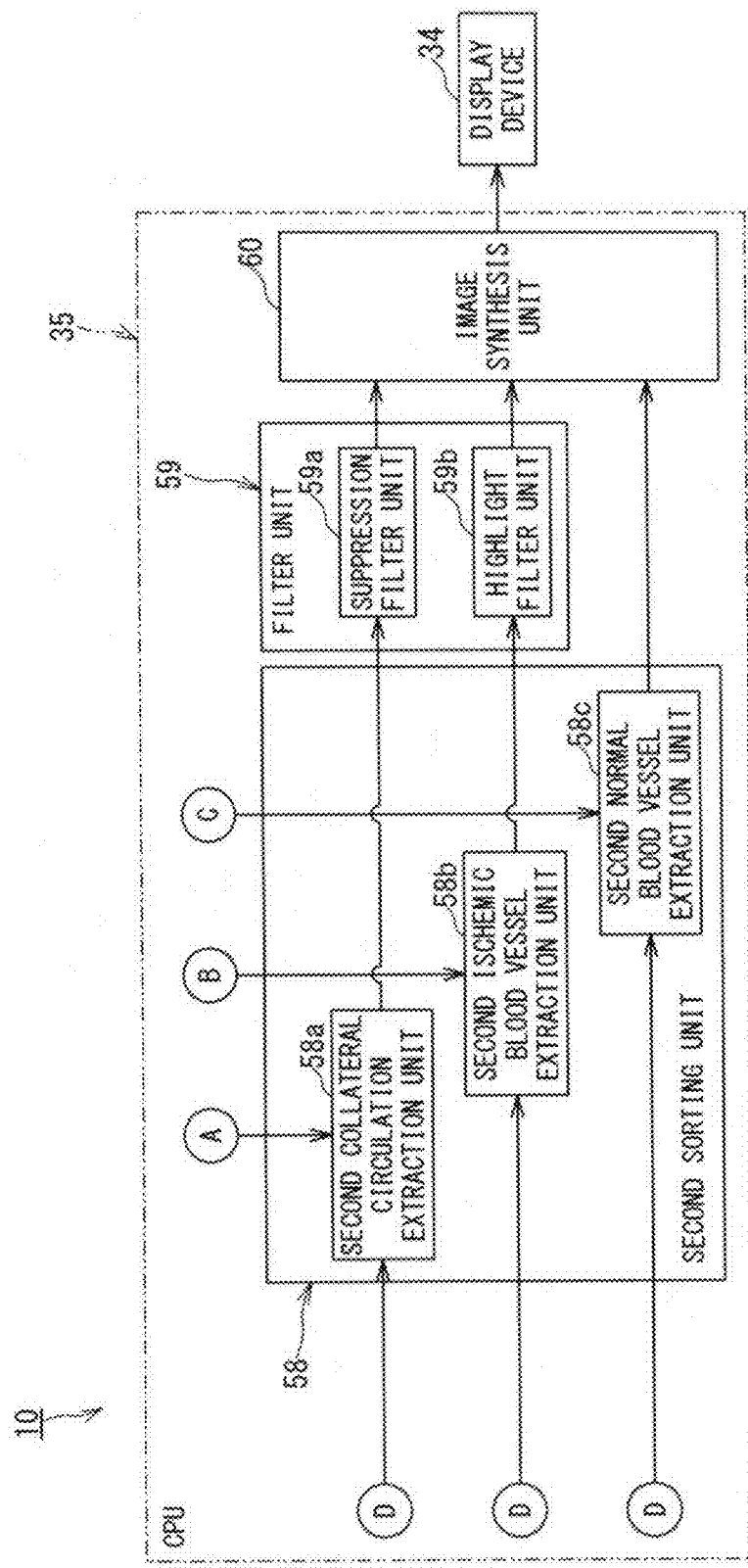
FIG. 3 is a block diagram showing functions of the angiographic apparatus in the medical image processing system according to the first embodiment.

FIGS. 2 and 3 are block diagrams showing functions of the angiographic apparatus 10 in the medical image processing system 1 according to the first embodiment.

As shown in FIGS. 2 and 3, when the CPU 35 shown in FIG. 1 executes a program, the angiographic apparatus 10 functions as an angiographic image acquisition unit 51, a volume data generation unit 52, a cerebral blood vessel extraction unit 53, a first sorting unit 54, an angiographic imaging control unit 55, a raysum fluoroscopic image generation unit 56, an alignment processing unit 57, a second sorting unit 58, a filter unit 59, and an image synthesis unit 60. Although each of the component members 51 through 60 shown in FIGS. 2 and 3 is described as the functions of the CPU 35, the present invention is not limited to this structure. Each of the component members 51 through 60 may be a hardware device included in the angiographic apparatus 10.

Figure 4:
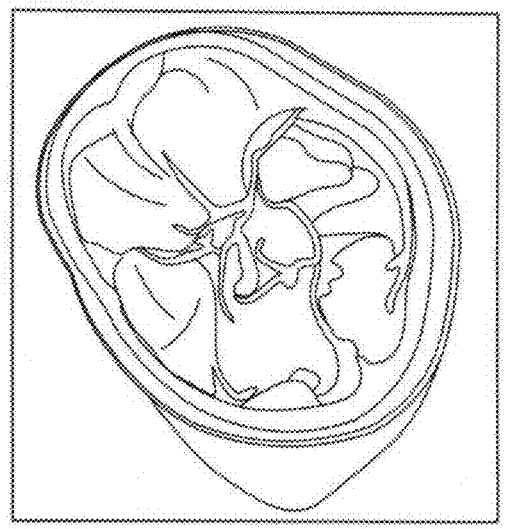
FIG. 4 is a diagram showing an example of an angiographic image (CT image)

Referring to FIG. 2, the angiographic image acquisition unit 51 has a function to acquire data of angiographic images (including non-contrast enhanced MRA images obtained without a contrast agent) collected by medical diagnostic imaging apparatuses such as X-ray CT apparatuses, MRI apparatuses and contrast-enhanced X-ray image diagnostic apparatuses via a storage device such as the HDD 37 or the network N, and the communication controller 39. An example of an angiographic image (CT image) is shown in FIG. 4.

The volume data generation unit 52 has a function to three-dimensionally reconstruct an angiographic image acquired by the angiographic image acquisition unit 51 to generate volume data for three-dimensional image processing.

Figure 5:
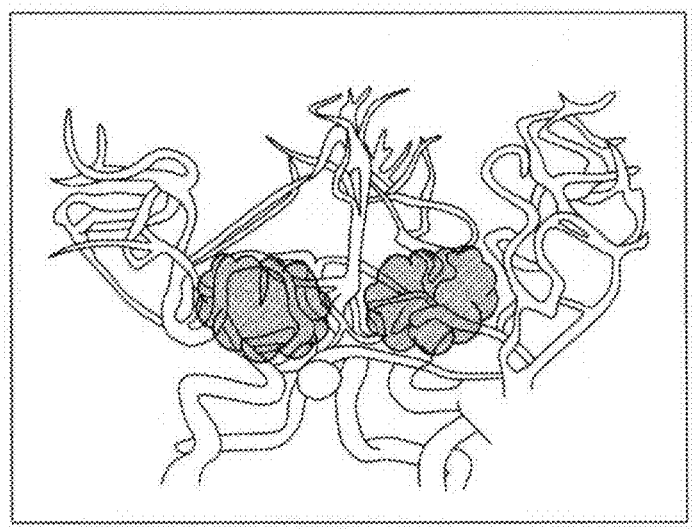
FIG. 5 is a diagram showing an example of a rendering image of the cerebral blood vessels.

The cerebral blood vessel extraction unit 53 has a function to extract data on cerebral blood vessels from the volume data generated by the volume data generation unit 52. An example of a rendering image of the cerebral blood vessels extracted by the cerebral blood vessel extraction unit 53 is shown in FIG. 5.

The first sorting unit 54 has a function to sort the cerebral blood vessels into collateral circulations, ischemic blood vessels, and normal blood vessels based on the cerebral blood vessels extracted by the cerebral blood vessel extraction unit 53. The first sorting unit 54 has a first collateral circulation extraction unit 54a, a first ischemic blood vessel extraction unit 54b, and a first normal blood vessel extraction unit 54c.

Figure 6:
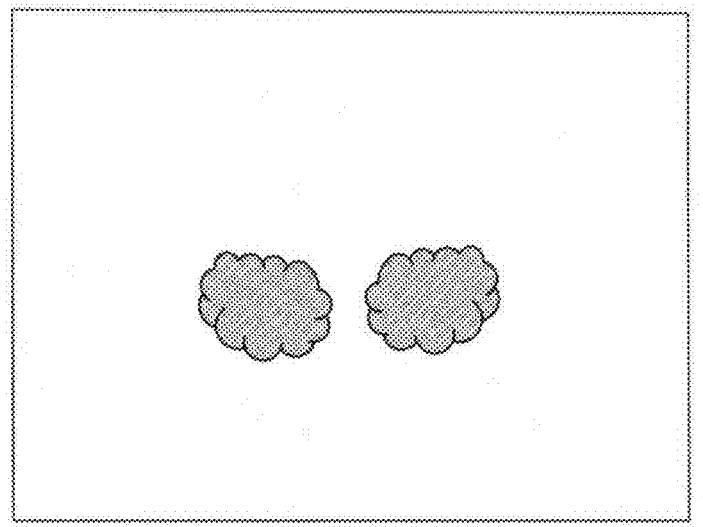
FIG. 6 is a diagram showing an example of a rendering image of collateral circulations.

The first collateral circulation extraction unit 54a has a function to extract, from the entire cerebral blood vessels extracted by the cerebral blood vessel extraction unit 53, data on collateral circulations as circulatory systems which, in the case of an occluded blood circulation in a main artery or a cardinal vein, act to maintain blood flow to an organization through a bypass formed by branching or side-branching and act to maintain return flow to the heart. An example of a rendering image of the collateral circulations extracted by the first collateral circulation extraction unit 54a is shown in FIG. 6.

Figure 7:
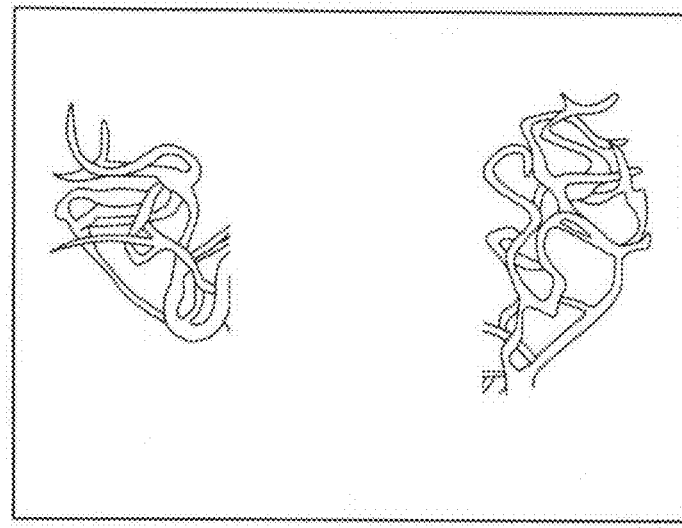
FIG. 7 is a diagram showing an example of a rendering image of ischemic blood vessels.

The first ischemic blood vessel extraction unit 54b has a function to extract data on ischemic blood vessels, which are blood vessels having a lowered blood flow rate on a downstream side, based on the entire cerebral blood vessels extracted by the cerebral blood vessel extraction unit 53 and the collateral circulations extracted by the first collateral circulation extraction unit 54a. An example of a rendering image of the ischemic blood vessels extracted by the first ischemic blood vessel extraction unit 54b is shown in FIG. 7.

Figure 8:
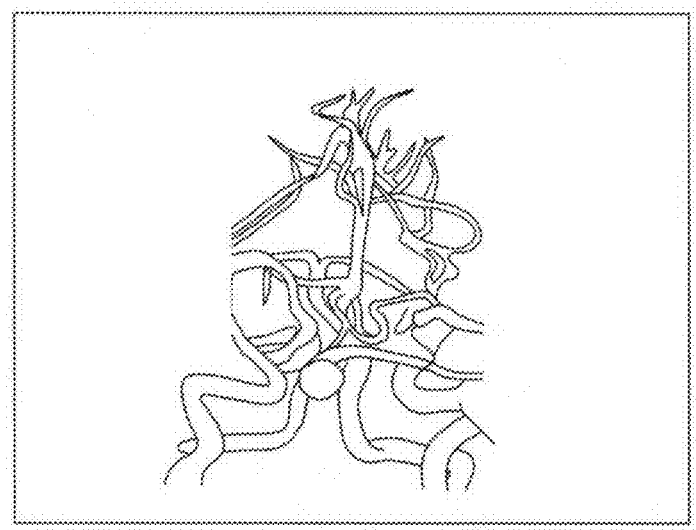
FIG. 8 is a diagram showing an example of a rendering image of normal blood vessels.

The first normal blood vessel extraction unit 54c has a function to extract data on normal blood vessels, based on the entire cerebral blood vessels extracted by the cerebral blood vessel extraction unit 53, the collateral circulations extracted by the first collateral circulation extraction unit 54a, and the ischemic blood vessels extracted by the first ischemic blood vessel extraction unit 54b. An example of a rendering image of the normal blood vessels extracted by the first normal blood vessel extraction unit 54c is shown in FIG. 8.

Although a description has been given of the first sorting unit 54 that executes extracting processing in order of the collateral circulations, the ischemic blood vessels, and the normal blood vessels, the present invention is not limited thereto. Each of the extraction sections 54a to 54c in the first sorting unit 54 extracts collateral circulations, ischemic blood vessels, and normal blood vessels as a region having a highest existence probability based on comparison with three-dimensional Atlas of the human body, estimation with feature values, or estimation with a morphological filter. Atlas is form data on a target internal organ generated from a plurality of image data sets through statistic approach and learning. Generally, Atlas includes only normal structures, and therefore, it cannot be used for abnormal structures like collateral circulations as a target.

Figure 9:
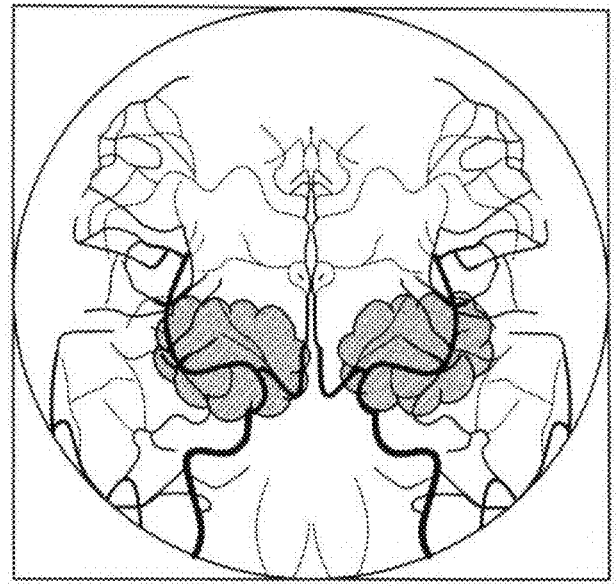
FIG. 9 is a diagram showing an example of a contrast-enhanced X-ray image.

The angiographic imaging control unit 55 has a function to control, once a contrast agent catheter is inserted into the patient P, the high-voltage generator 26, the injector 28, and the drive mechanism 27 through the system controller 40 so as to perform angiography imaging which is to irradiate a head of the patient P with an X-ray, a dosage of which is based on determined imaging conditions, and a function to acquire a contrast-enhanced X-ray image (projection image) generated by the image generation circuit 31. An example of the contrast-enhanced X-ray image acquired by the angiography imaging control unit 55 is shown in FIG. 9.

The raysum fluoroscopic image generation unit 56 has a function to apply perspective projection (perspective) and raysum rendering (raysum rendering) processes to the volume data generated by the volume data generation unit 52 to generate raysum fluoroscopic image data.

The alignment processing unit 57 has a function to align the raysum fluoroscopic image generated by the raysum fluoroscopic image generation unit 56 and the contrast-enhanced X-ray image sequentially acquired by the angiographic imaging control unit 55 generally in real time. The alignment by the alignment processing unit 57 is not limited to that with use of the raysum fluoroscopic image and the contrast-enhanced X-ray image. For example, the alignment processing unit 57 may employ a method which uses image-attached information such as an imaging position and range attached to the data.

Referring to FIG. 3, the second sorting unit 58 has a function to sort respective blood vessels from the contrast-enhanced X-ray image aligned by the alignment processing unit 57 shown in FIG. 2, based on the collateral circulations in the volume data extracted by the first collateral circulation extraction unit 54a shown in FIG. 2, the ischemic blood vessels in the volume data extracted by the first ischemic blood vessel extraction unit 54b shown in FIG. 2, and the normal blood vessels in the volume data extracted by the first normal blood vessel extraction unit 54c shown in FIG. 2. The second sorting unit 58 has a second collateral circulation extraction unit 58a, a second ischemic blood vessel extraction unit 58b, and a second normal blood vessel extraction unit 58c.

Figure 10:
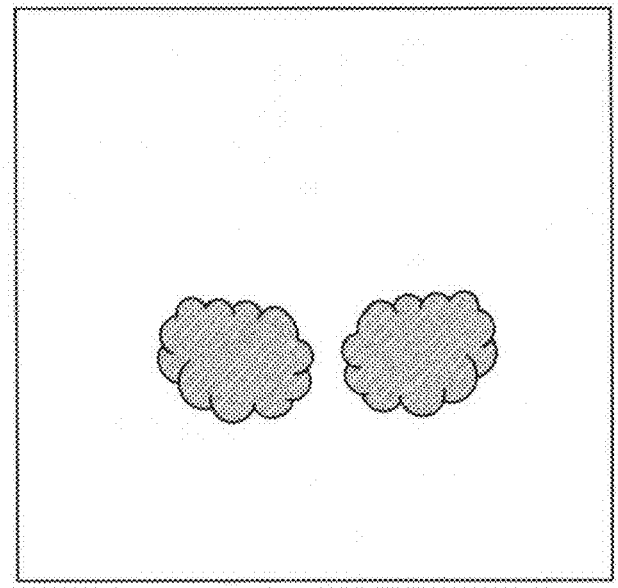
FIG. 10 is a diagram showing an example of an image of collateral circulations.

The second collateral circulation extraction unit 58a has a function to extract collateral circulation data from the contrast-enhanced X-ray image aligned by the alignment processing unit 57 shown in FIG. 2, based on the collateral circulations in the volume data extracted by the first collateral circulation extraction unit 54a shown in FIG. 2. An example of an image of the collateral circulations extracted by the second collateral circulation extraction unit 58a is shown in FIG. 10.

Figure 11:
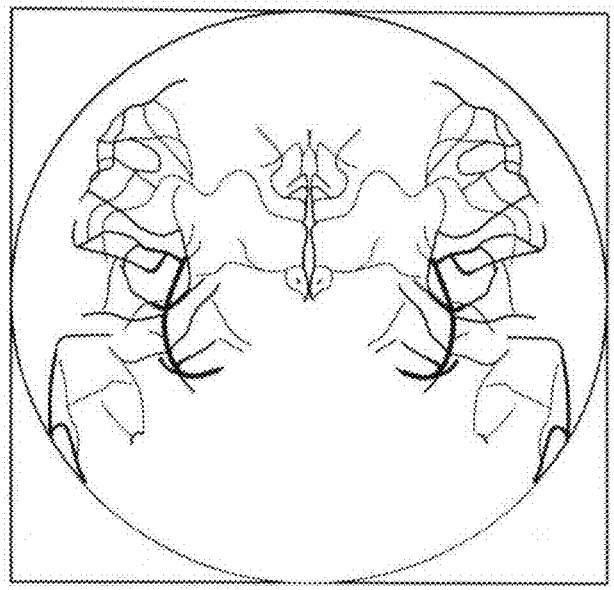
FIG. 11 is a diagram showing an example of an image of ischemic blood vessels.

The second ischemic blood vessel extraction unit 58b has a function to extract ischemic blood vessel data from the contrast-enhanced X-ray image aligned by the alignment processing unit 57 shown in FIG. 2, based on the ischemic blood vessels in the volume data extracted by the first ischemic blood vessel extraction unit 54b shown in FIG. 2. An example of an image of the ischemic blood vessels extracted by the second ischemic blood vessel extraction unit 58b is shown in FIG. 11.

Figure 12:
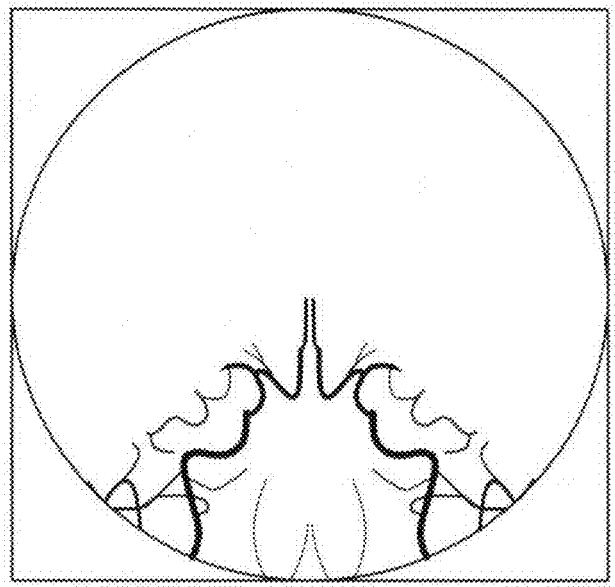
FIG. 12 is a diagram showing an example of an image of normal blood vessels.

The second normal blood vessel extraction unit 58c has a function to extract normal blood vessel data from the contrast-enhanced X-ray image aligned by the alignment processing unit 57 shown in FIG. 2, based on the normal blood vessels in the volume data extracted by the first normal blood vessel extraction unit 54c shown in FIG. 2. An example of an image of the normal blood vessels extracted by the second normal blood vessel extraction unit 58c is shown in FIG. 12.

The filter unit 59 has a suppression filter unit 59a and a highlight filter unit 59b. When a highlight target is ischemic blood vessels, the suppression filter unit 59a of the filter unit 59 performs processing to suppress display of the collateral circulations, while the highlight filter unit 59b performs processing to highlight the ischemic blood vessels. In a not shown case where a highlighted target is a collateral circulation, the suppression filter unit 59a of the filter unit 59 performs display suppression of the ischemic blood vessels, while the highlight filter unit 59b performs processing to highlight the collateral circulations.

Figure 13:
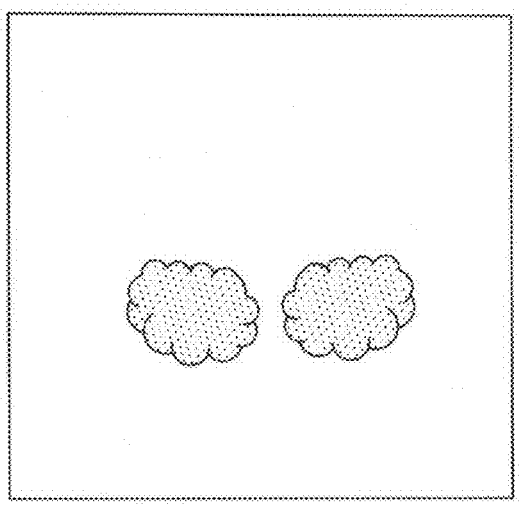
FIG. 13 is a diagram showing an example of an image of collateral circulations subjected to the suppression filter.

The suppression filter unit 59a has a function to apply a suppression filter to suppress display of the collateral circulations in the contrast-enhanced X-ray image. This function is used in the case where collateral circulations in the contrast-enhanced X-ray image extracted by the second collateral circulation extraction unit 58a have abnormally developed vessel structures and ischemic blood vessels are a highlighted target. An example of an image of the collateral circulations subjected to the suppression filter by the suppression filter unit 59a is shown in FIG. 13.

The highlight filter unit 59b has a function to apply a highlight filter to highlight display of ischemic blood vessels in the contrast-enhanced X-ray image. This function is used in the case where ischemic blood vessels in the contrast-enhanced X-ray image extracted by the second ischemic blood vessel extraction unit 58b have normal vessel structures and ischemic blood vessels are a highlighted target.

The image synthesis unit 60 has a function to apply different image processes to the collateral circulations filtered by the suppression filter unit 59a, the ischemic blood vessels filtered by the highlight filter unit 59b, and the normal blood vessels extracted by the second normal blood vessel extraction unit 58c, to perform synthesis processing thereof, and to sequentially generate synthesized image data. The image synthesis unit 60 is set so that the filtered collateral circulations, ischemic blood vessels and the normal blood vessels have independent display attributes (such as display/non-display status, color, and transparency), and then sequentially generates synthesized image data. The synthesized image also includes synthesized text information and scales of various parameters or the like. The synthesized image generated by the image synthesis unit 60 is sent to the display device 34 as video signals and is displayed through the display device 34. The synthesized image is displayed generally in real time by the image synthesis unit 60 as a reproduced moving image.

Figure 14:
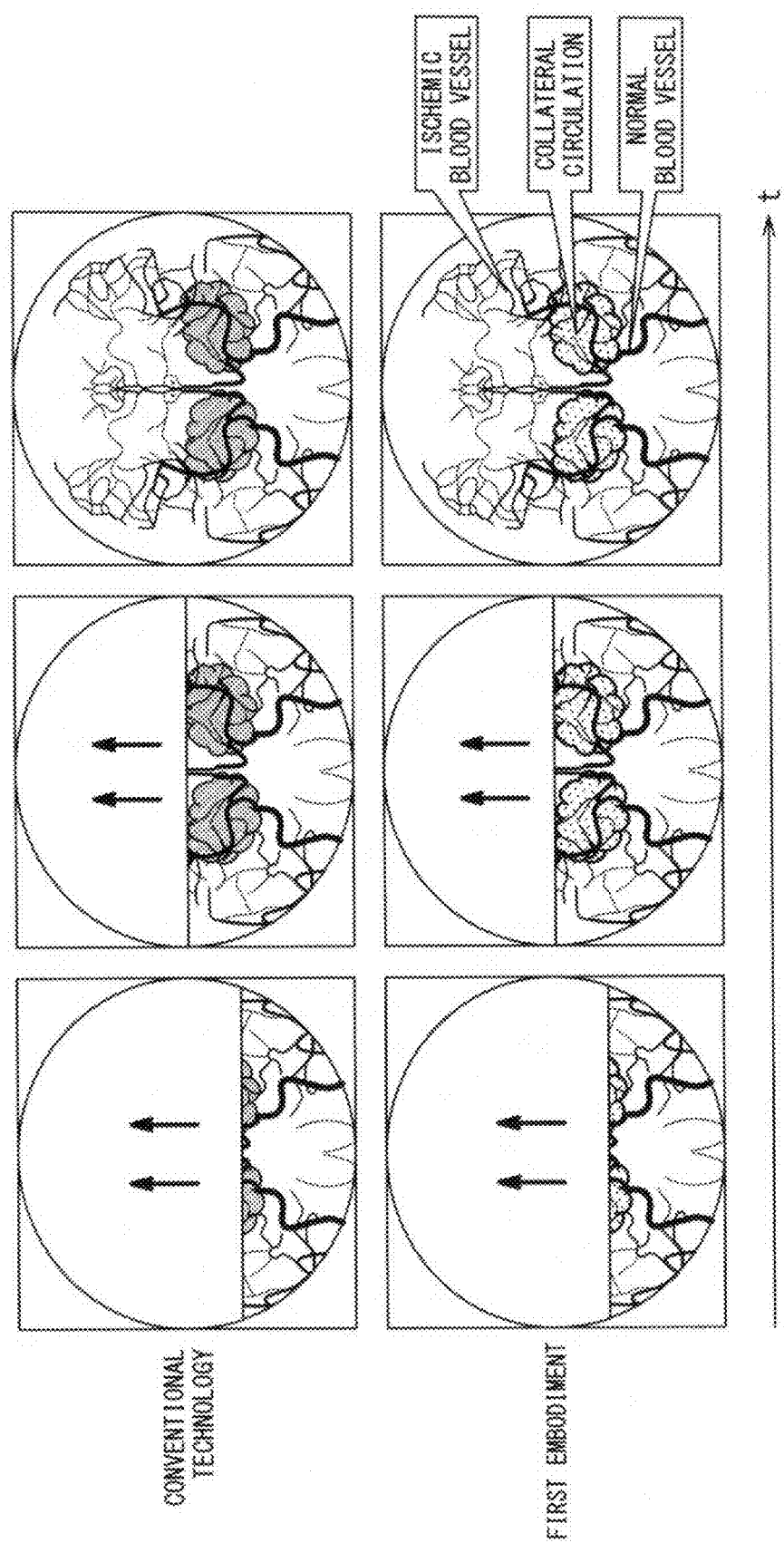
FIG. 14 is a diagram showing contrast-enhanced X-ray images according to the conventional technology in an upper row and showing an example of synthesized images according to the first embodiment in a lower row.

FIG. 14 is a diagram showing contrast-enhanced X-ray images according to the conventional technology in an upper row and showing an example of the synthesized images according to the first embodiment in a lower row. The contrast-enhanced X-ray images and the synthesized images shown in FIG. 14 are arrayed in a time-series order from the left-hand side to the right-hand side.

As shown in the upper row of FIG. 14, a contrast agent inflow area spreads out with elapse of time in the contrast-enhanced X-ray images according to the conventional technology. Since collateral circulations, ischemic blood vessels, and normal blood vessels are not sorted, the collateral circulations, the ischemic blood vessels, and the normal blood vessels are displayed with an identical display attribute.

As shown in the lower row of FIG. 14, a contrast agent inflow area also spreads out with elapse of time in the synthesized image of the first embodiment. However, while the lower row of FIG. 14 shows an example in which collateral circulations, ischemic blood vessels, and normal blood vessels are displayed with an identical display attribute for the sake of convenience, it is also possible to display the collateral circulations, the ischemic blood vessels, and the normal blood vessels with different display attributes.

According to the medical image processing system 1 in the first embodiment, cerebral blood vessels in a contrast-enhanced X-ray image are sorted into collateral circulations and ischemic blood vessels, the respective blood vessels are subjected to different image processes and filtering, and the respective blood vessels are then displayed with independent display attributes, so that vessel structures are reproduced and displayed in real time as visible images.

Second Embodiment

A second embodiment is different from the first embodiment in the point that collateral circulations and ischemic blood vessels are displayed with a rendering image of volume data by being synthesized therewith.

Figure 15:
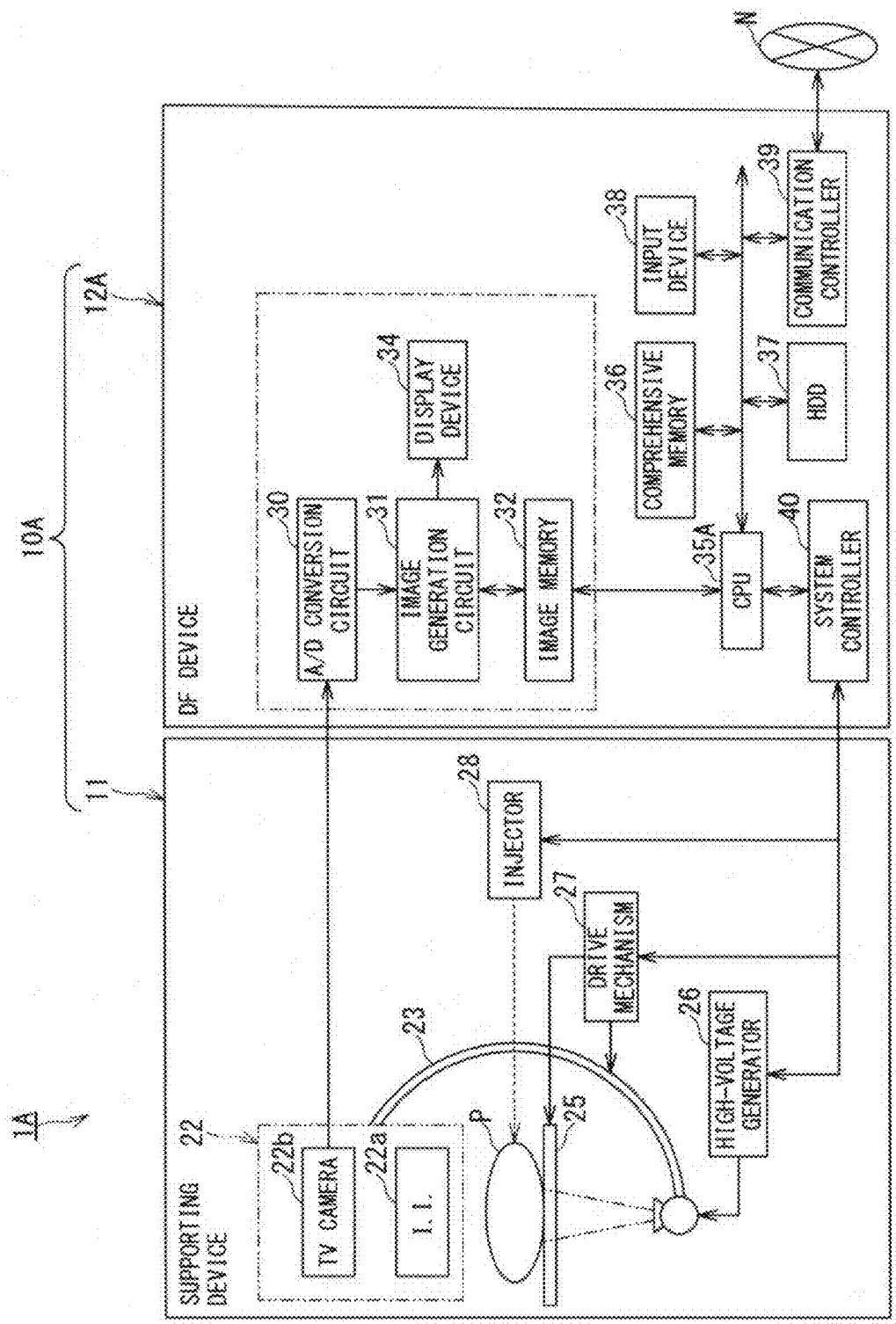
FIG. 15 is a schematic diagram showing an example of a structure of a medical image processing system according to a second embodiment.

FIG. 15 is a schematic diagram showing an example of a structure of a medical image processing system according to the second embodiment.

FIG. 15 shows a medical image processing system 1A according to the second embodiment. The medical image processing system 1A includes an angiographic apparatus 10A as an X-ray image diagnostic apparatus. The angiographic apparatus 10A is mainly constituted of a supporting device 11 and a DF device 12A.

The DF device 12A, which is structured by a computer as a base, can mutually communicate with a network N such as a hospital-based LAN. The DF device 12A is mainly constituted of hardware devices such as an A/D conversion circuit 30, an image generation circuit 31, an image memory 32, a display device 34, a CPU 35A as a processor, a comprehensive memory 36, an HDD 37, an input device 38, a communication controller 39, and a system controller 40. The CPU 35A is mutually connected with respective hardware components that constitute the DF device 12A via a bus as a common signal transmission line. The DF device 12A may include a recording medium drive (not shown).

Since a structure of the CPU 35A is similar to that of the CPU 35 explained with reference to FIG. 1, a description thereof will be omitted.

In the medical image processing system 1A according to the second embodiment shown in FIG. 15, component members identical to those of the medical image processing system 1 according to the first embodiment shown in FIG. 1 are designated by identical reference numerals to omit a description thereof.

Figure 16:
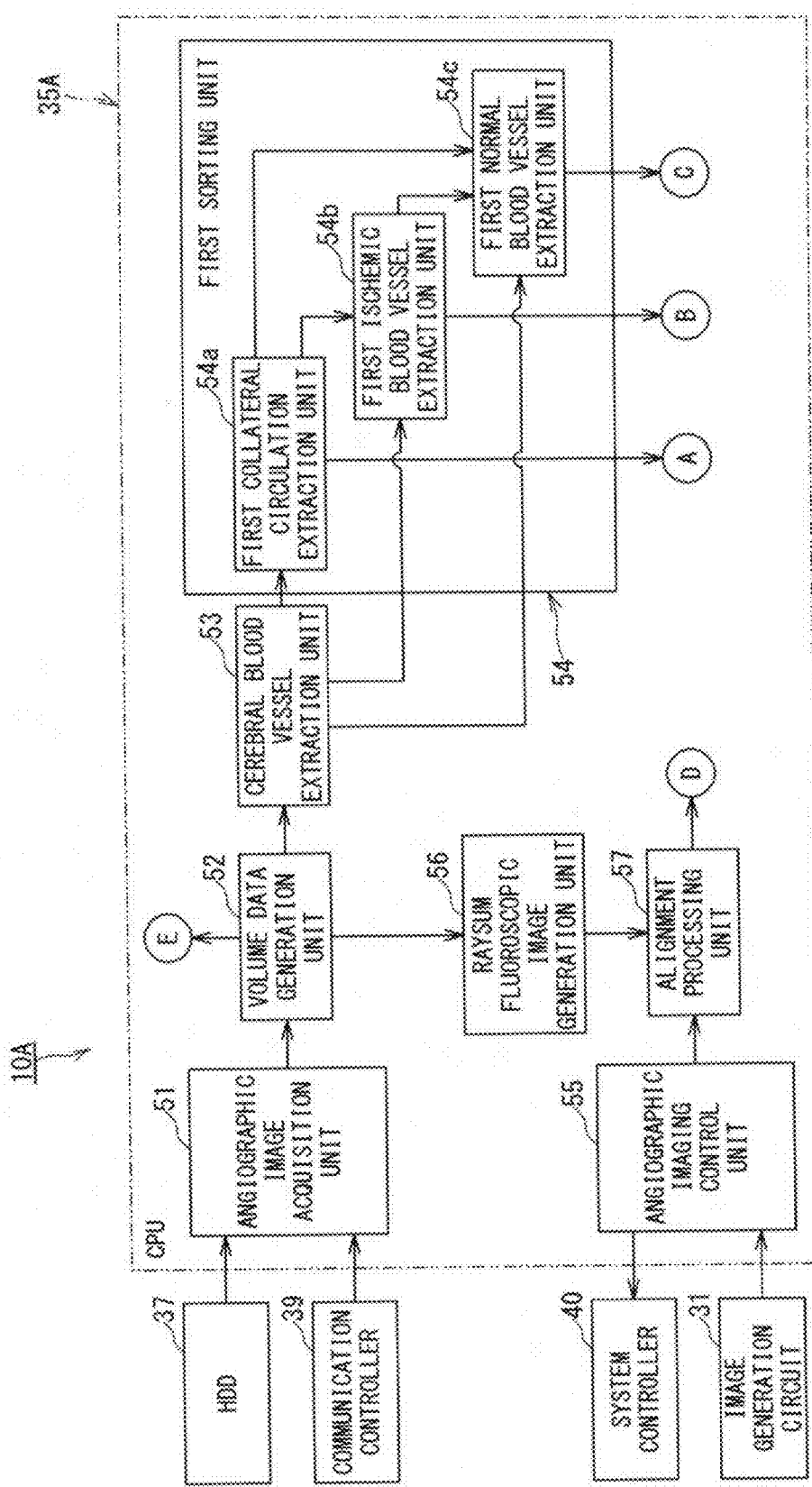
FIG. 16 is a block diagram showing functions of an angiographic apparatus in the medical image processing system according to the second embodiment.
Figure 17:
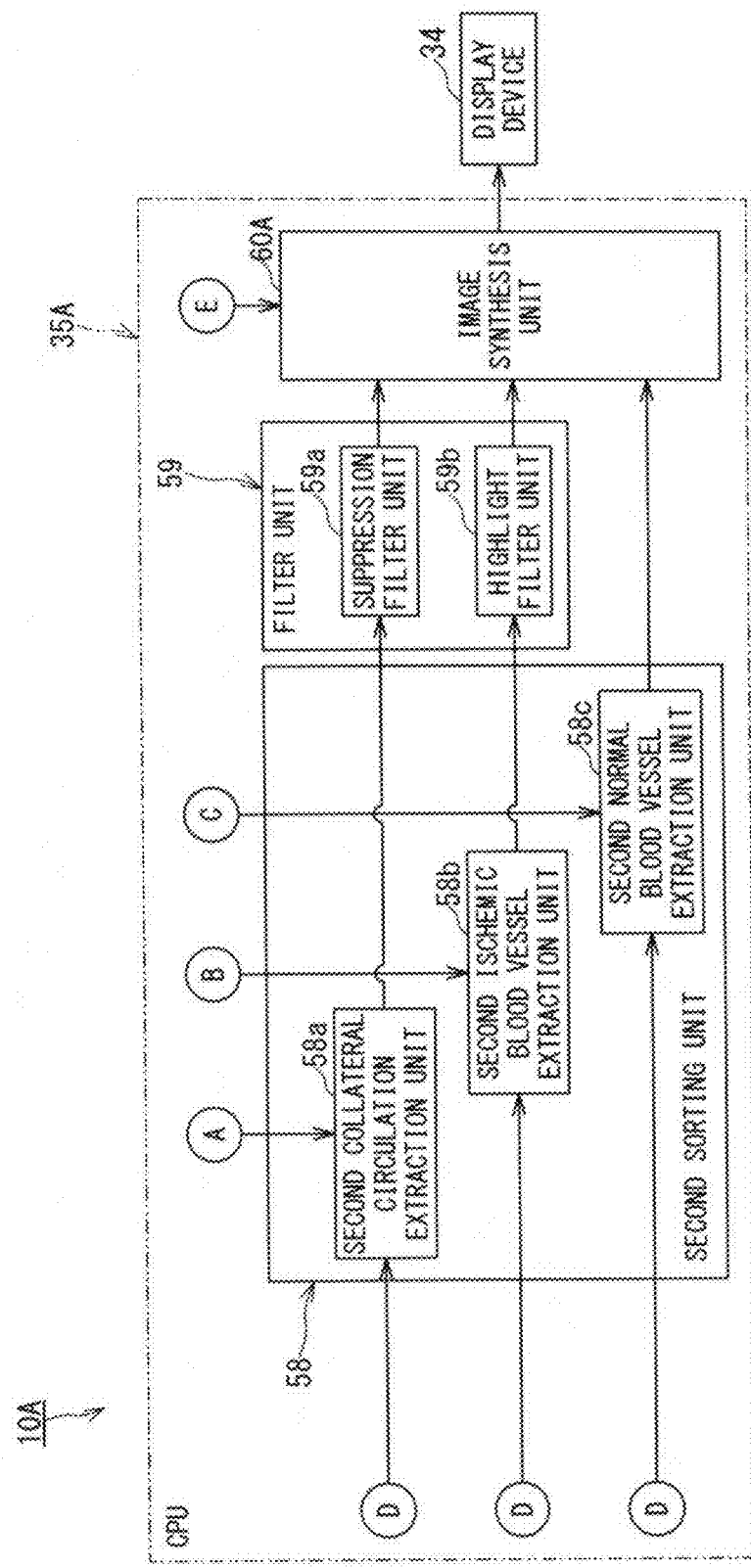
FIG. 17 is a block diagram showing functions of the angiographic apparatus in the medical image processing system according to the second embodiment.

FIGS. 16 and 17 are block diagrams showing functions of the angiographic apparatus 10A in the medical image processing system 1A according to the second embodiment.

As shown in FIGS. 16 and 17, when the CPU 35A shown in FIG. 15 executes a program, the angiographic apparatus 10A functions as an angiographic image acquisition unit 51, a volume data generation unit 52, a cerebral blood vessel extraction unit 53, a first sorting unit 54, an angiographic imaging control unit 55, a raysum fluoroscopic image generation unit 56, an alignment processing unit 57, a second sorting unit 58, a filter unit 59, and an image synthesis unit 60A. Although each of the component members 51 through 60A shown in FIGS. 16 and 17 is described as functions of the CPU 35A, the present invention is not limited thereto. Each of the component members 51 through 60A may be a hardware device included in the angiographic apparatus 10A.

In the medical image processing system 1A according to the second embodiment shown in FIGS. 16 and 17, functions identical to those of the medical image processing system 1 according to the first embodiment shown in FIGS. 2 and 3 are designated by identical reference numerals to omit a description thereof.

Referring to FIG. 17, the image synthesis unit 60A has a function to synthesize a rendering (including MPR) image based on volume data generated by the volume data generation unit 52 shown in FIG. 16, collateral circulations filtered by a suppression filter unit 59a, ischemic blood vessels filtered by a highlight filter unit 59b, and normal blood vessels extracted by a second normal blood vessel extraction unit 58c, to provide a setting so that each blood vessel has an independent display attribute, and to sequentially generate synthesized image data. The synthesized image also includes synthesized text information and scales of various parameters or the like. The synthesized image generated by the image synthesis unit 60A is sent to the display device 34 as video signals and is displayed through the display device 34. The synthesized image is displayed generally in real time by the image synthesis unit 60A as a reproduced moving image.

The synthesized image generated by the image synthesis unit 60A can be used as a load map for use at the time of inserting a treatment catheter.

According to the medical image processing system 1A in the second embodiment, cerebral blood vessels in a contrast-enhanced X-ray image are sorted into collateral circulations and ischemic blood vessels, the respective blood vessels are subjected to different image processes and filtering, and the respective blood vessels are then displayed with independent display attributes, so that vessel structures are reproduced and displayed in real time as visible images at the time of the catheter treatment with the angiographic apparatus 10A.

Third Embodiment

A third embodiment is different from the first and second embodiments in a structure when a treatment catheter is inserted into a patient under fluoroscopic guidance.

Figure 18:
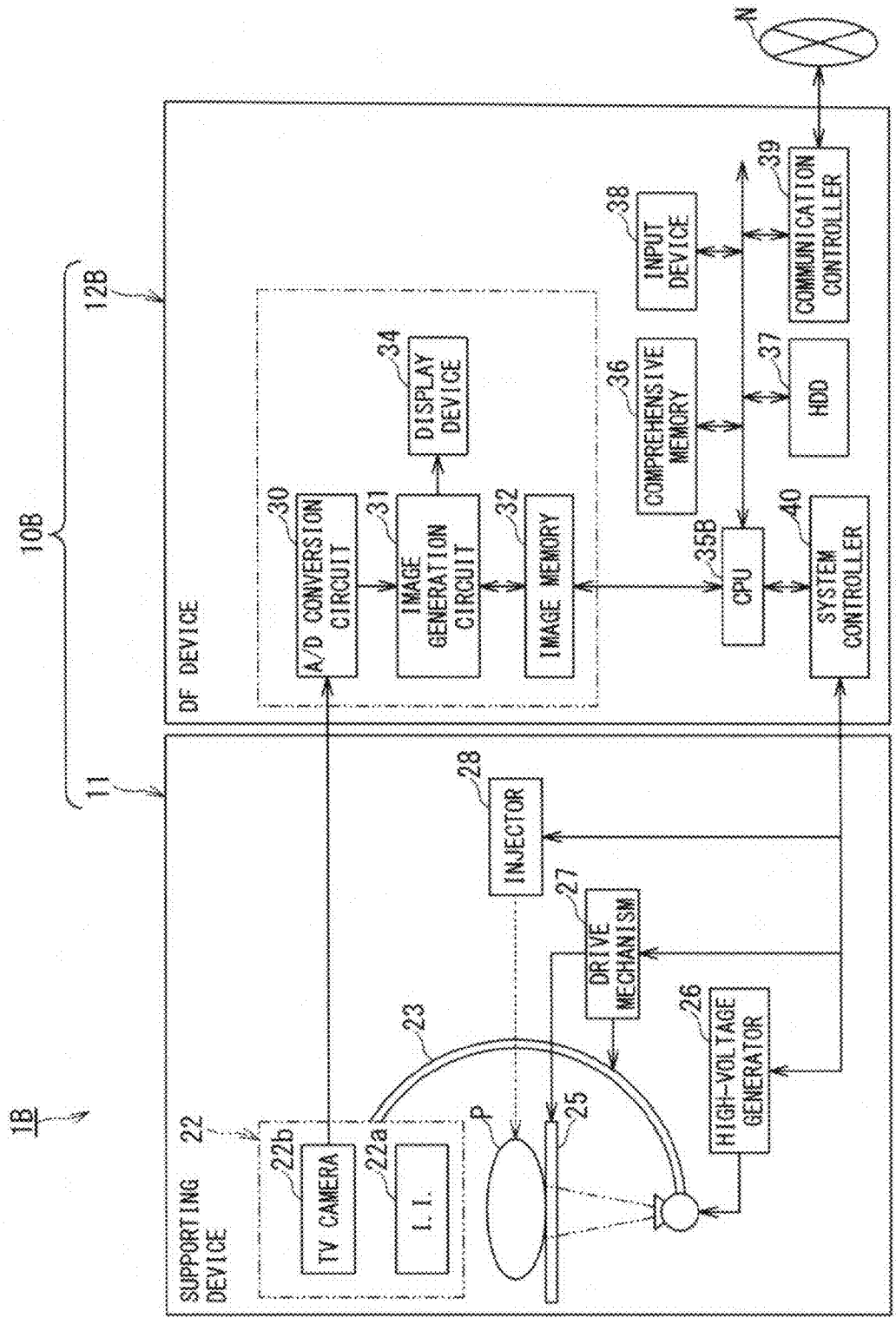
FIG. 18 is a schematic diagram showing an example of a structure of a medical image processing system according to a third embodiment.

FIG. 18 is a schematic diagram showing one example of a structure of a medical image processing system according to the third embodiment.

FIG. 18 shows a medical image processing system 1B according to the third embodiment. The medical image processing system 1B includes an angiographic apparatus 10B as an X-ray image diagnostic apparatus. The angiographic apparatus 10B is mainly constituted of a supporting device 11 and a DF device 12B.

The DF device 12B, which is structured by a computer as a base, can mutually communicate with a network N such as a hospital-based LAN. The DF device 12B is mainly constituted of hardware devices such as an A/D conversion circuit 30, an image generation circuit 31, an image memory 32, a display device 34, a CPU 35B as a processor, a comprehensive memory 36, an HDD 37, an input device 38, a communication controller 39, and a system controller 40. The CPU 35B is mutually connected with respective hardware components that constitute the DF device 12B via a bus as a common signal transmission line. The DF device 12B may include a recording medium drive (not shown).

Since a structure of the CPU 35B is similar to that of the CPU 35 explained with reference to FIG. 1, a description thereof will be omitted.

In the medical image processing system 1B according to the third embodiment shown in FIG. 18, component members identical to those of the medical image processing system 1 according to the first embodiment shown in FIG. 1 are designated by identical reference numerals to omit a description thereof.

Figure 19:
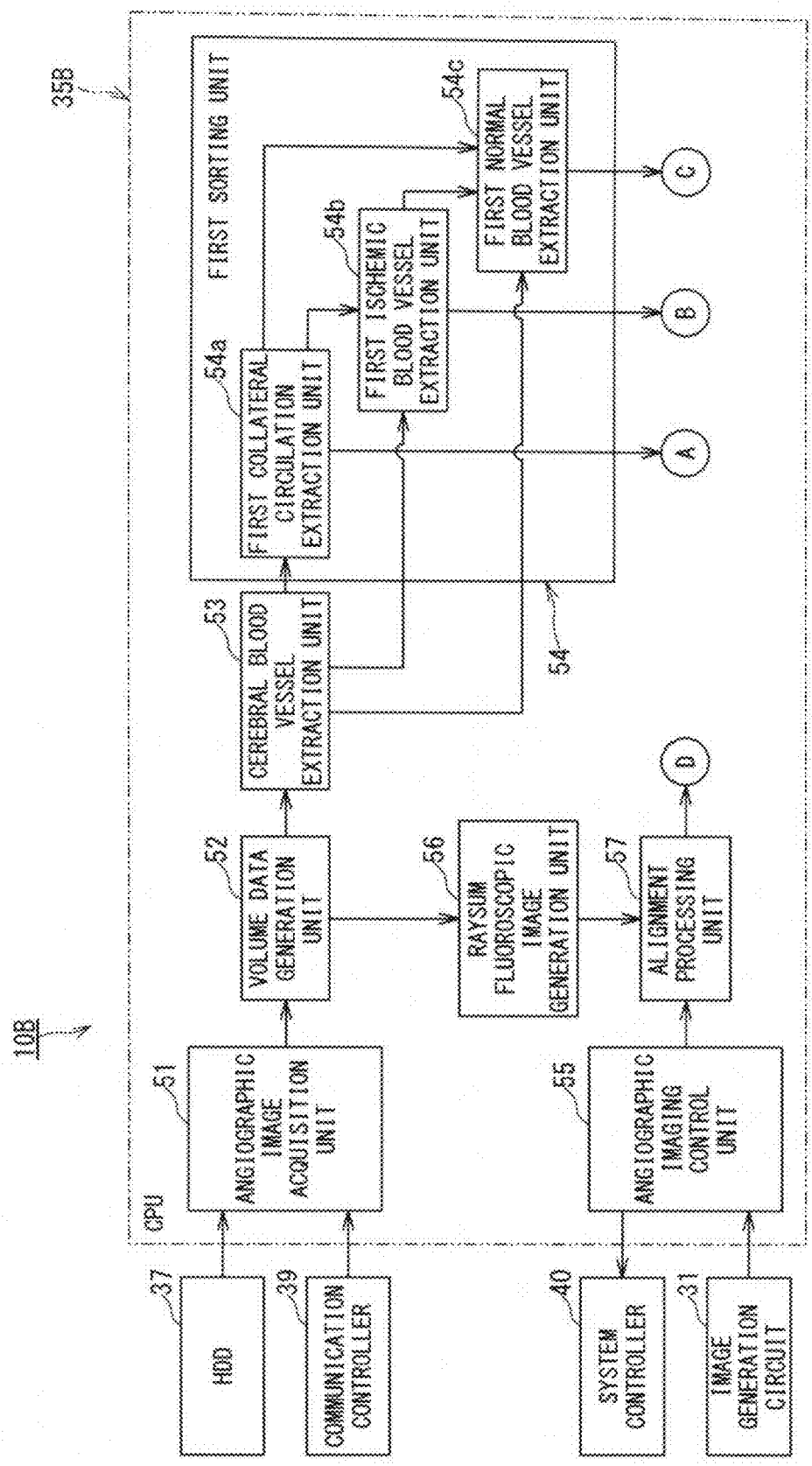
FIG. 19 is a block diagram showing functions of an angiographic apparatus in the medical image processing system according to the third embodiment.
Figure 20:
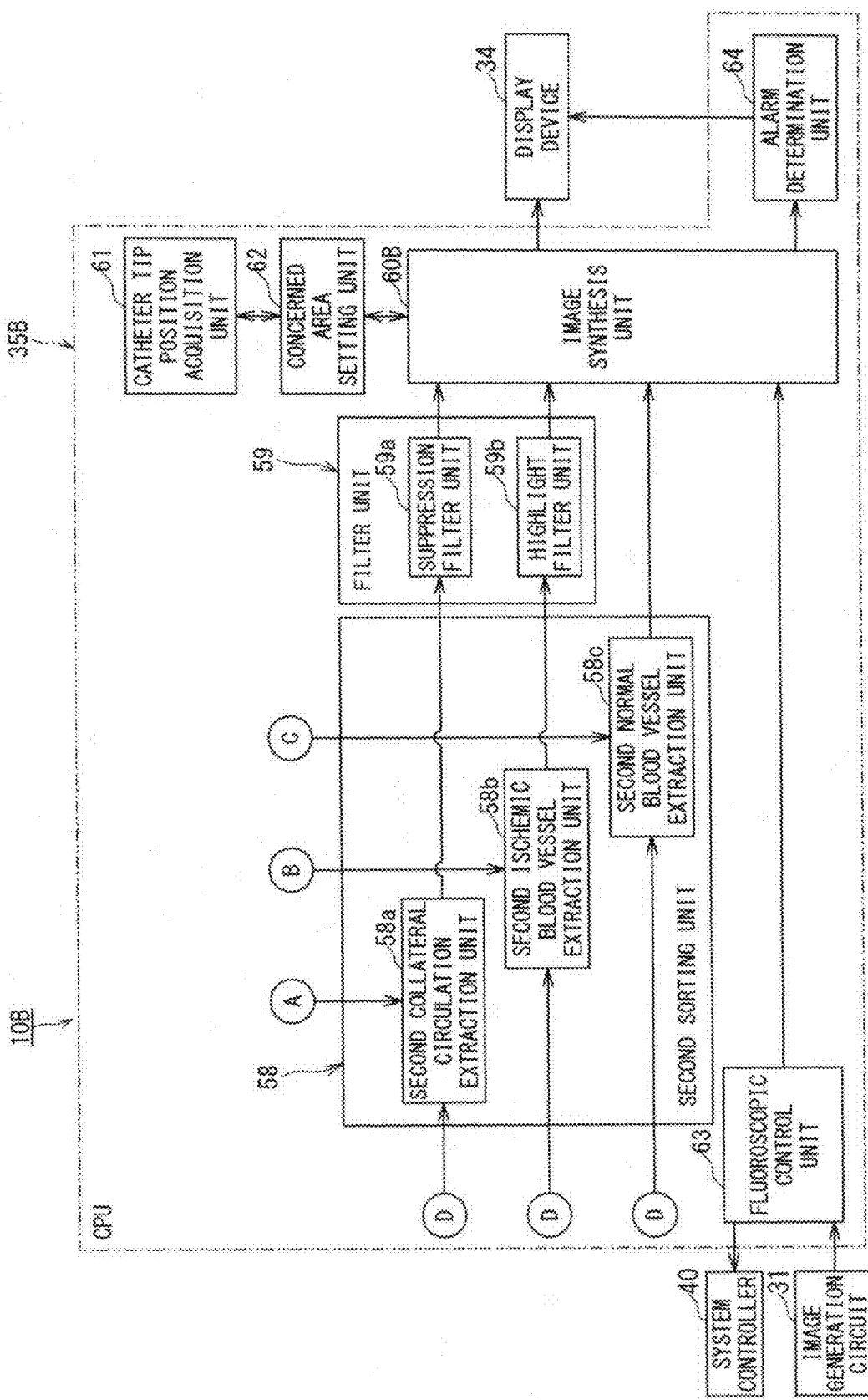
FIG. 20 is a block diagram showing functions of the angiographic apparatus in the medical image processing system according to the third embodiment.

FIGS. 19 and 20 are block diagrams showing functions of the angiographic apparatus 10B in the medical image processing system 1B according to the third embodiment.

As shown in FIGS. 19 and 20, when the CPU 35B shown in FIG. 18 executes a program, the angiographic apparatus 10B functions as an angiographic image acquisition unit 51, a volume data generation unit 52, a cerebral blood vessel extraction unit 53, a first sorting unit 54, an angiographic imaging control unit 55, a raysum fluoroscopic image generation unit 56, an alignment processing unit 57, a second sorting unit 58, a filter unit 59, an image synthesis unit 60B, a catheter tip position acquisition unit 61, a concerned area setting unit 62, a fluoroscopic control unit 63, and an alarm determination unit 64. Although each of the component members 51 through 64 shown in FIGS. 19 and 20 is described as functions of the CPU 35B, the present invention is not limited thereto. Each of the component members 51 through 64 may be a hardware device included in the angiographic apparatus 10B.

In the medical image processing system 1B according to the third embodiment shown in FIGS. 19 and 20, functions identical to those of the medical image processing system 1 according to the first embodiment shown in FIGS. 2 and 3 are designated by identical reference numerals to omit a description thereof.

Referring to FIG. 20, the image synthesis unit 60B has a function to synthesize collateral circulations filtered by a suppression filter unit 59a, ischemic blood vessels filtered by a highlight filter unit 59b, and normal blood vessels extracted by a second normal blood vessel extraction unit 58c, to provide a setting so that each blood vessel has an independent display attribute, and to sequentially generate synthesized image data. The synthesized image also includes synthesized text information and scales of various parameters or the like. The synthesized image generated by the image synthesis unit 60B is sent to the display device 34 as video signals and is displayed through the display device 34. The synthesized image is displayed generally in real time by the image synthesis unit 60B as a reproduced moving image.

The catheter tip position acquisition unit 61 has a function to sequentially detect a current position of a treatment catheter tip identified with a three-dimensional position sensor (not shown) or the like.

The concerned area setting unit 62 has a function to set a concerned area on a synthesized image generated by the image synthesis unit 60B. For example, when it is desired to avoid insertion of a treatment catheter into collateral circulations, the concerned area setting unit 62 sets a collateral circulation selected by an operator as a concerned area on the synthesized image displayed through the display device 34.

The fluoroscopic control unit 63 has a function to control a high voltage generator 26 and a drive mechanism 27 through the system controller 40 so as to execute fluoroscopy that is to irradiate the head of the patient P with a relatively low dosage of an X-ray based on determined fluoroscopic conditions and a function to acquire a fluoroscopic image generated by the image generation circuit 31. An operator inserts the treatment catheter into an involved part of the patient P under fluoroscopic guidance by the fluoroscopic control unit 63.

The image synthesis unit 60B has a function to synthesize the above-mentioned synthesized image and a fluoroscopic image sequentially acquired by the fluoroscopic control unit 63 to generate a fluoroscopic synthesized image in sequence. The fluoroscopic synthesized image also includes synthesized text information and scales of various parameters or the like. The fluoroscopic synthesized image generated by the image synthesis unit 60B is sent to the display device 34 as video signals and is displayed through the display device 34. The fluoroscopic synthesized image is displayed generally in real time by the image synthesis unit 60B as a reproduced moving image. The above-mentioned synthesized image and the serial fluoroscopic image may independently be displayed side by side through the display device 34 without being synthesized with each other.

The alarm determination unit 64 has a function to output a warning during real-time reproduction of a fluoroscopic synthesized image as a moving image, based on a relative positional relationship between a tip position of the treatment catheter detected by the catheter tip position acquisition unit 61 and a collateral circulation as a concerned area set by the concerned area setting unit 62. For example, in the case of detecting the treatment catheter during real-time reproduction of a fluoroscopic synthesized image as a moving image, the alarm determination unit 64 displays an alarm through the display device 34 if a distance between the tip position of the treatment catheter and the collateral circulation exceeds a threshold.

Figure 21:
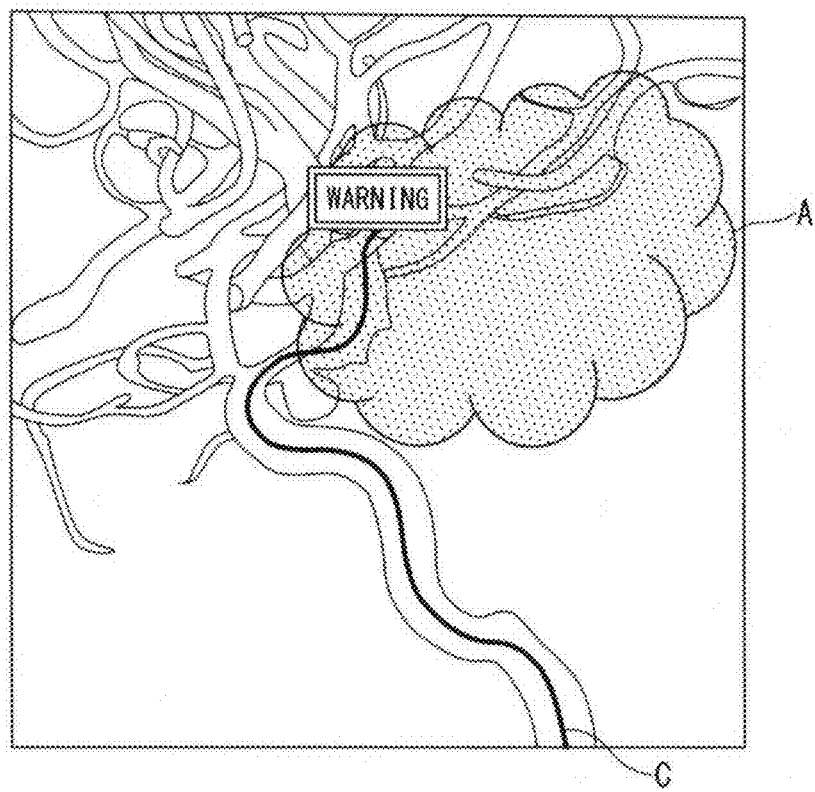
FIG. 21 is a diagram showing an example of an alarm display.

FIG. 21 is a diagram showing an example of an alarm display.

When a treatment catheter C enters into a collateral circulation A during real-time moving image reproduction by the image synthesis unit 60B as shown in FIG. 21, the alarm determination unit 64 detects the tip of the treatment catheter and issues an alarm through the display device 34. An alarming method is not limited to the method shown in FIG. 21. For example, the display attributes of the collateral circulation as a concerned area may be changed (blinked or the like) to inform an operator of the alarm.

The medical image processing system 1B urges a user to change a moving direction of the treatment catheter when a distance between the concerned area and the tip of the treatment catheter is decreased during fluoroscopic guidance. In the case of treating a collateral circulation by coil embolization, the concerned area setting unit 62 may set the collateral circulation as a concerned area, and then the image synthesis unit 60B may guide the treatment catheter in a direction toward the concerned area.

According to the medical image processing system 1B in the third embodiment, cerebral blood vessels in a contrast-enhanced X-ray image are sorted into collateral circulations and ischemic blood vessels, the respective blood vessels are subjected to different image processes and filtering, and the respective blood vessels are displayed with independent display attributes, so that vessel structures are reproduced and displayed in real time as visible images at the time of the catheter treatment by the angiographic apparatus 10B.

Fourth Embodiment

Since an object of a fourth embodiment is to perform post-imaging processing of a diagnostic imaging workstation or the like, the fourth embodiment does not have functions to collect and process images in real time unlike the first to third embodiments.

Figure 22:
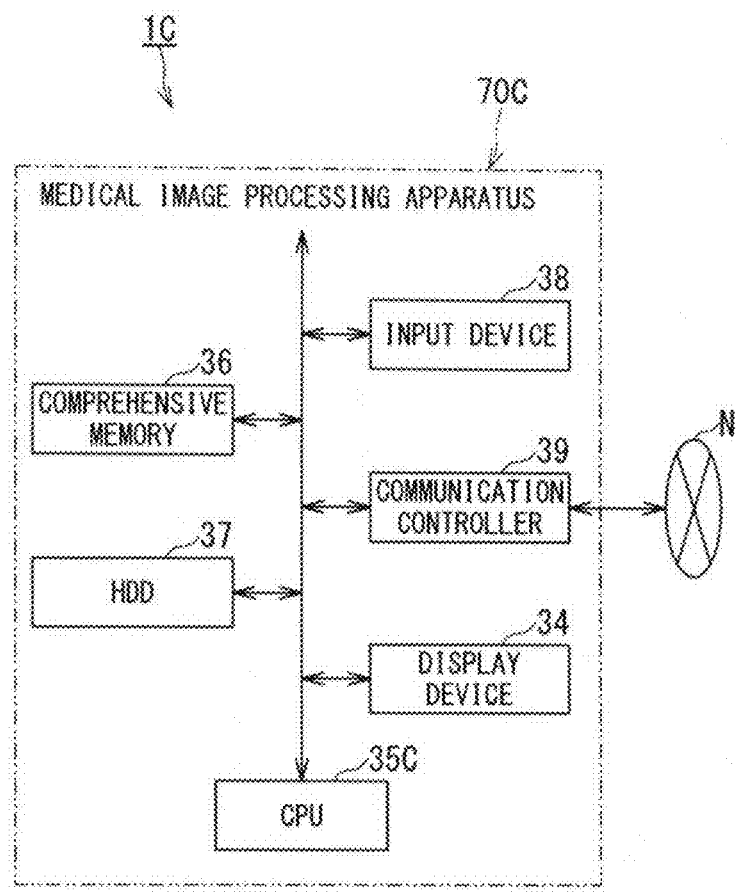
FIG. 22 is a schematic diagram showing an example of a structure of a medical image processing system according to a fourth embodiment.

FIG. 22 is a schematic diagram showing an example of a structure of a medical image processing system according to the fourth embodiment.

FIG. 22 shows a medical image processing system 1C according to the fourth embodiment. The medical image processing system 1C includes a medical image processing apparatus 70C. The medical image processing apparatus 70C, which is structured by a computer as a base, can mutually communicate with a network N. The medical image processing apparatus 70C is mainly constituted of basic hardware devices such as a display device 34, a CPU 35C, a comprehensive memory 36, an HDD 37, an input device 38, and a communication controller 39. The CPU 35C is mutually connected with respective hardware components that constitute the medical image processing apparatus 70C via a bus as a common signal transmission line. The medical image processing apparatus 70C may include a storage medium drive (not shown).

In the medical image processing system 10 according to the fourth embodiment shown in FIG. 22, component members identical to those of the medical image processing system 1 according to the first embodiment shown in FIG. 1 are designated by identical reference numerals to omit a description thereof.

Figure 23:
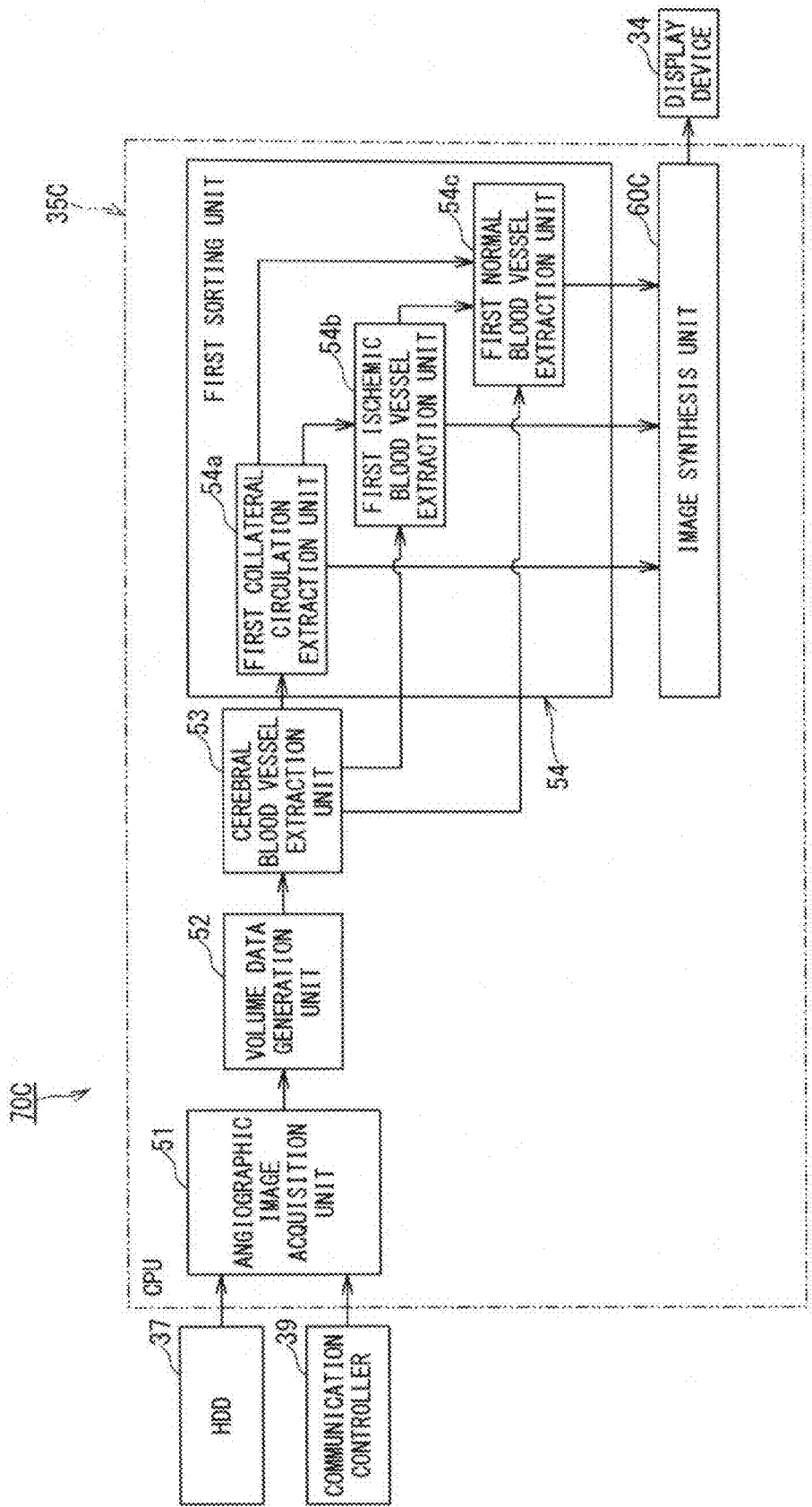
FIG. 23 is a block diagram showing functions of a medical image processing apparatus in the medical image processing system according to the fourth embodiment.

FIG. 23 is a block diagram showing functions of the medical image processing apparatus 70C in the medical image processing system 1C according to the fourth embodiment.

When the CPU 35C shown in FIG. 22 executes a program, the medical image processing apparatus 70C functions as an angiographic image acquisition unit 51, a volume data generation unit 52, a cerebral blood vessel extraction unit 53, a first sorting unit 54, and an image synthesis unit 60C as shown in FIG. 23. Although each of the component members 51 through 54 and 60C shown in FIG. 23 is described as functions of the CPU 35C, the present invention is not limited thereto. Each of the component members 51 through 54 and 60C may be a hardware device included in the medical image processing apparatus 70C.

In the medical image processing system 10 according to the fourth embodiment shown in FIG. 23, functions identical to those of the medical image processing system 1 according to the first embodiment shown in FIGS. 2 and 3 are designated by identical reference numerals to omit a description thereof.

The image synthesis unit 60C has a function to synthesize collateral circulations in the volume data extracted by a first collateral circulation extraction unit 54a, ischemic blood vessels in the volume data extracted by a first ischemic blood vessel extraction unit 54b, and normal blood vessels extracted by a first normal blood vessel extraction unit 54c, to provide a setting so that each blood vessel has an independent display attribute and to perform rendering with the setting so as to generate synthesized image data. The synthesized image also includes synthesized text information and scales of various parameters or the like. The synthesized image generated by the image synthesis unit 60C is sent to the display device 34 as video signals and is displayed through the display device 34.

According to the medical image processing system 1C in the fourth embodiment, cerebral blood vessels in a contrast-enhanced X-ray image are sorted into collateral circulations and ischemic blood vessels and each vessel is displayed with an independent display attribute, so that vessel structures can be displayed as a visible image.

Fifth Embodiment

Since an object of a fifth embodiment is to perform post-imaging processing of a diagnostic imaging workstation or the like as in the forth embodiment, the fifth embodiment does not have functions to collect and process images in real time.

Figure 24:
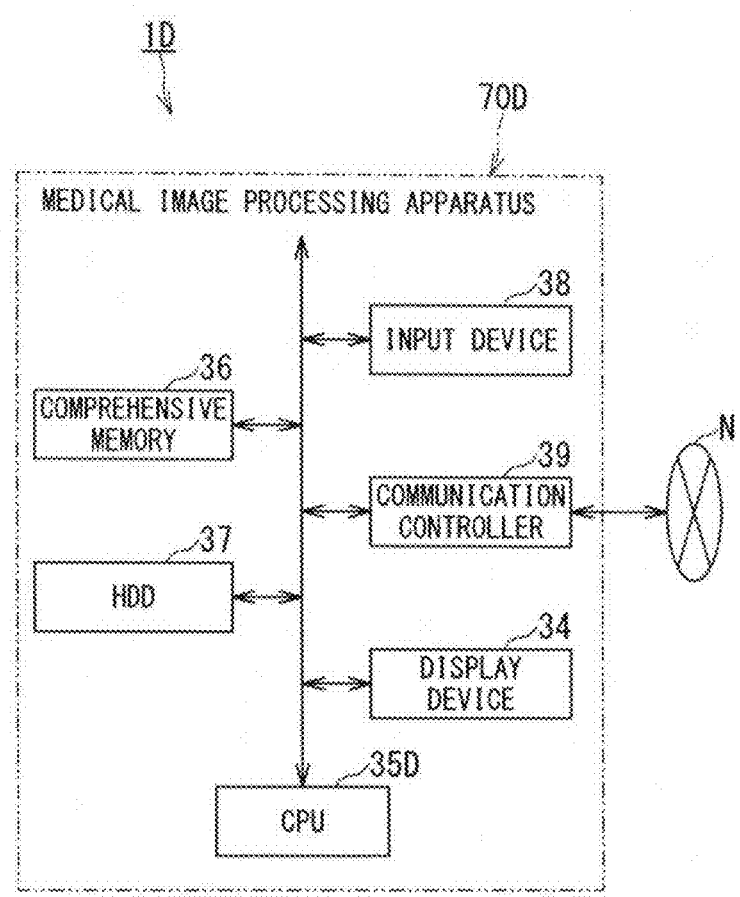
FIG. 24 is a schematic diagram showing an example of a structure of a medical image processing system according to a fifth embodiment.

FIG. 24 is a schematic diagram showing one example of a structure of a medical image processing system according to the fifth embodiment.

FIG. 24 shows a medical image processing system 1D according to the fifth embodiment. The medical image processing system 1D includes a medical image processing apparatus 70D. The medical image processing apparatus 70D, which is structured by a computer as a base, can mutually communicate with a network N. The medical image processing apparatus 70D is mainly constituted of basic hardware devices such as a display device 34, a CPU 35D, a comprehensive memory 36, an HDD 37, an input device 38, and a communication controller 39. The CPU 35D is mutually connected with respective hardware components that constitute the medical image processing apparatus 70D via a bus as a common signal transmission line. The medical image processing apparatus 70D may include a storage medium drive (not shown).

In the medical image processing system 1D according to the fifth embodiment shown in FIG. 24, component members identical to those of the medical image processing system 1 according to the first embodiment shown in FIG. 1 are designated by identical reference numerals to omit a description thereof.

Figure 25:
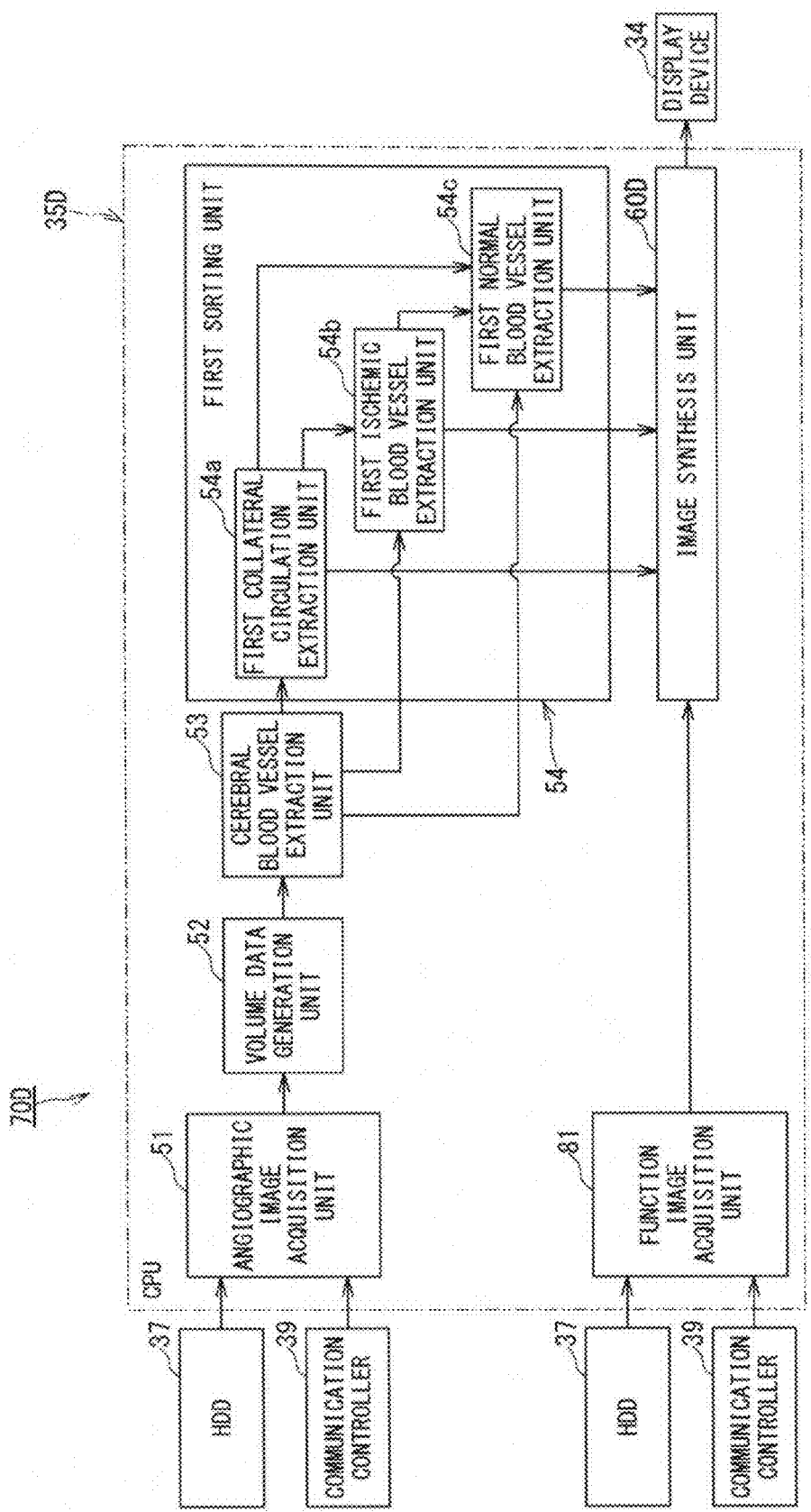
FIG. 25 is a block diagram showing functions of a medical image processing apparatus in the medical image processing system according to the fifth embodiment.

FIG. 25 is a block diagram showing functions of the medical image processing apparatus 70D in the medical image processing system 1D according to the fifth embodiment.

When the CPU 35D shown in FIG. 24 executes a program, the medical image processing apparatus 70D functions as an angiographic image acquisition unit 51, a volume data generation unit 52, a cerebral blood vessel extraction unit 53, a first sorting unit 54, an image synthesis unit 60D, and a function image acquisition unit 81 as shown in FIG. 25. Although each of the component members 51 through 54, 60D and 81 shown in FIG. 25 is described as functions of the CPU 35D, the present invention is not limited thereto. Each of the component members 51 through 54, 60D and 81 may be a hardware device included in the medical image processing apparatus 70D.

In the medical image processing system 1D according to the fifth embodiment shown in FIG. 25, functions identical to those of the medical image processing system 1 according to the first embodiment shown in FIGS. 2 and 3 are designated by identical reference numerals to omit a description thereof.

The function image acquisition sections 81 has a function to acquire function images on a region including a brain collected by medical diagnostic imaging apparatuses such as X-ray CT apparatuses, MRI apparatuses and PET (positron emission tomography) apparatuses, or to acquire data on processed images such as perfusion images obtained by analyzing the function images by post-processing, via a storage device such as the HDD 37 or the network N, and the communication controller 39.

The image synthesis unit 60D has a function to synthesize collateral circulations in the volume data extracted by a first collateral circulation extraction unit 54a, ischemic blood vessels in the volume data extracted by a first ischemic blood vessel extraction unit 54b, and normal blood vessels in the volume data extracted by a first normal blood vessel extraction unit 54c, to provide a setting so that each blood vessel has an independent display attribute, to perform rendering, and to further synthesize the function image acquired by the function image acquisition unit 81 to generate synthesized image data. The synthesized image also includes synthesized text information and scales of various parameters or the like. The synthesized image generated by the image synthesis unit 60D is sent to the display device 34 as video signals and is displayed through the display device 34. The synthesized image generated by the image synthesis unit 60D can present a relative positional relation between the function image, the collateral circulations and the ischemic blood vessels.

According to the medical image processing system 1D in the fifth embodiment, cerebral blood vessels in a contrast-enhanced X-ray image are sorted into collateral circulations and ischemic blood vessels, and each vessel is displayed with an independent display attribute, so that vessel structures can be displayed as a visible image.

Sixth Embodiment

Since an object of a sixth embodiment is to perform post-imaging processing of a diagnostic imaging workstation or the like as in the fourth and fifth embodiments, the sixth embodiment does not have functions to collect and process images in real time.

Figure 26:
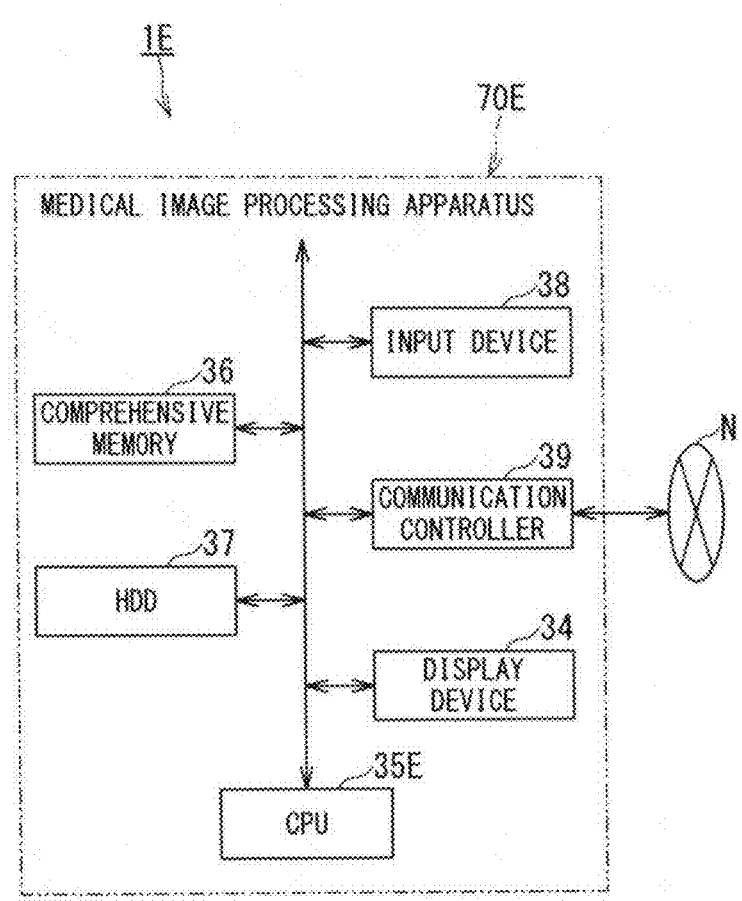
FIG. 26 is a schematic diagram showing an example of a structure of a medical image processing system according to a sixth embodiment.

FIG. 26 is a schematic diagram showing one example of a structure of a medical image processing system according to the sixth embodiment.

FIG. 26 shows a medical image processing system 1E according to the sixth embodiment. The medical image processing system 1E shows a medical image processing apparatus 70E. The medical image processing apparatus 70E, which is structured by a computer as a base, can mutually communicate with a network N. The medical image processing apparatus 70E is mainly constituted of basic hardware devices such as a display device 34, a CPU 35E, a comprehensive memory 36, an HDD 37, an input device 38, and a communication controller 39. The CPU 35E is mutually connected with respective hardware components that constitute the medical image processing apparatus 70E via a bus as a common signal transmission line. The medical image processing apparatus 70E may include a storage medium drive (not shown).

In the medical image processing system 1E according to the sixth embodiment shown in FIG. 26, component members identical to those of the medical image processing system 1 according to the first embodiment shown in FIG. 1 are designated by identical reference numerals to omit a description thereof.

Figure 27:
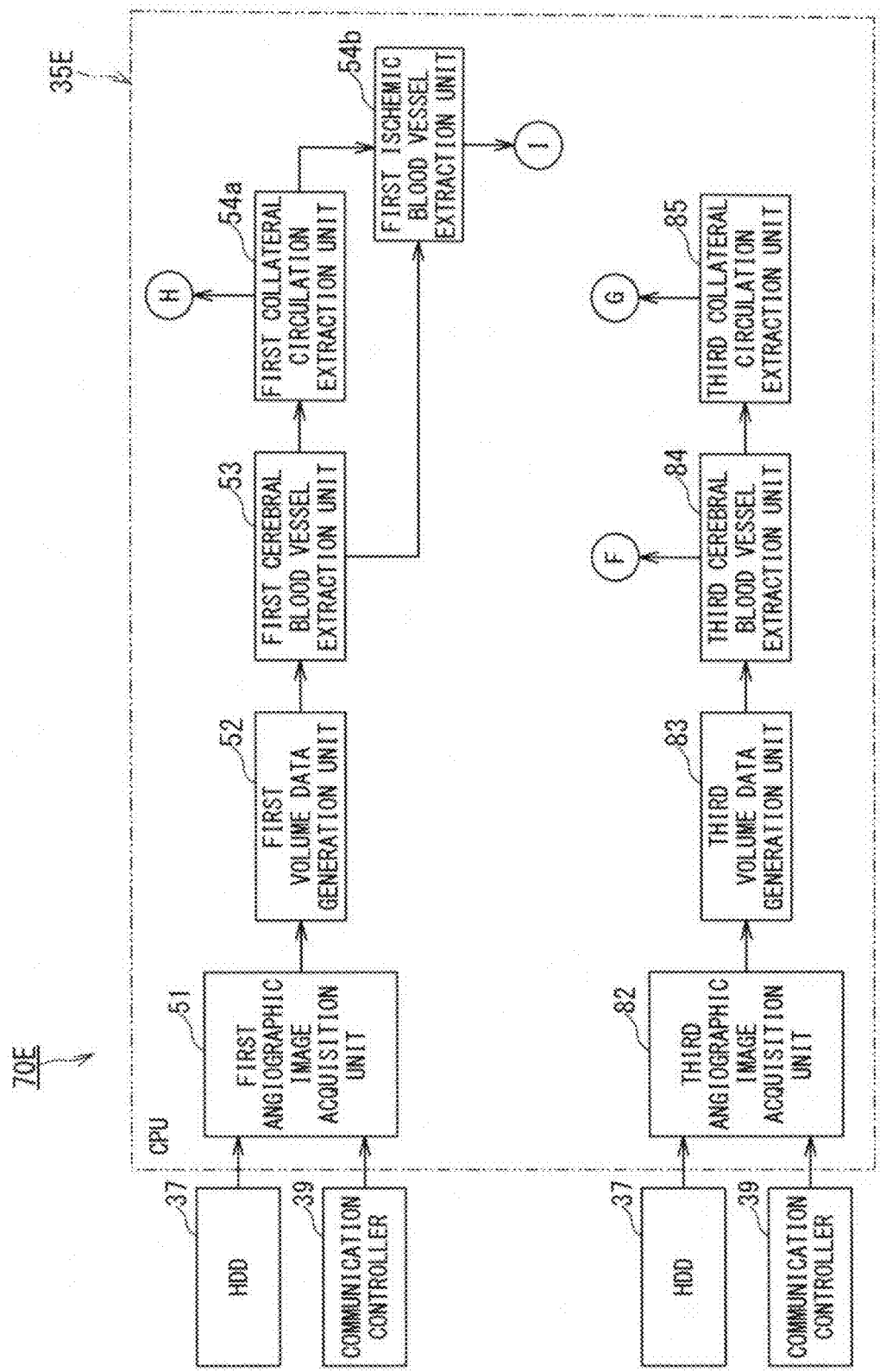
FIG. 27 is a block diagram showing functions of a medical image processing apparatus in the medical image processing system according to the sixth embodiment.
Figure 28:
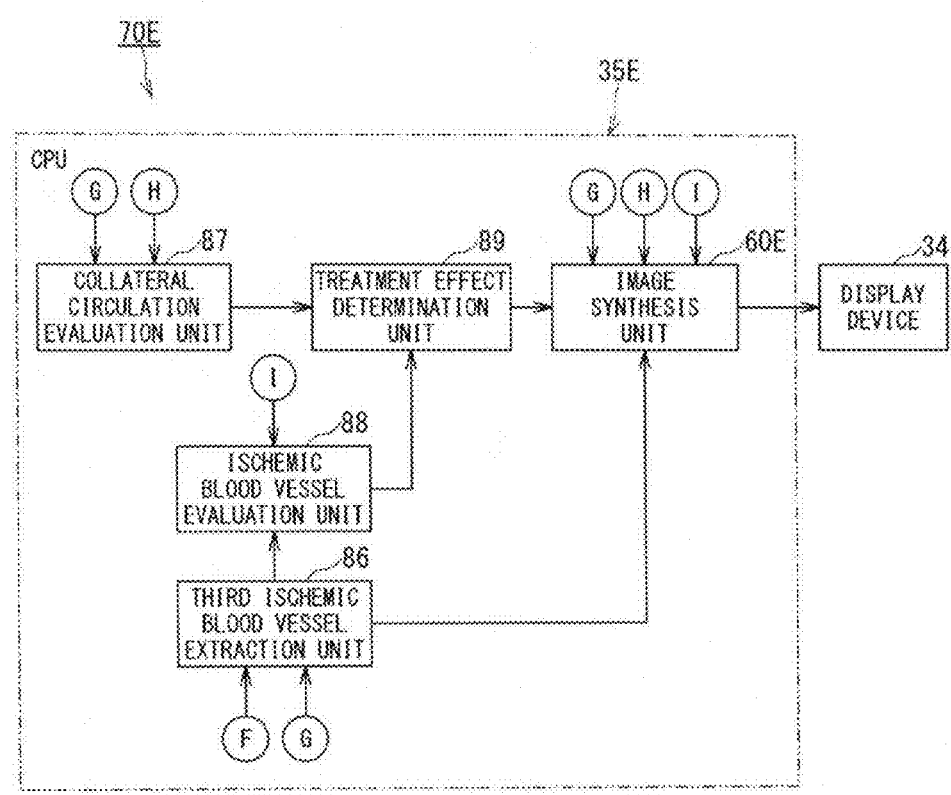
FIG. 28 is a block diagram showing functions of the medical image processing apparatus in the medical image processing system according to the sixth embodiment.

FIGS. 27 and 28 are block diagrams showing functions of the medical image processing apparatus 70E in the medical image processing system 1E according to the sixth embodiment.

When the CPU 35E shown in FIG. 26 executes a program, the medical image processing apparatus 70E functions, as shown in FIGS. 27 and 28, as a first angiographic image acquisition section (angiographic image acquisition section) 51, a first volume data generation section (volume data generation section) 52, a first cerebral blood vessel extraction section (cerebral blood vessel extraction section) 53, a first collateral circulation extraction unit 54a, a first ischemic blood vessel extraction unit 54b, an image synthesis unit 60E, a third angiographic image acquisition unit 82, a third volume data generation unit 83, a third cerebral blood vessel extraction unit 84, a third collateral circulation extraction unit 85, a third ischemic blood vessel extraction unit 86, a collateral circulation evaluation unit 87, an ischemic blood vessel evaluation unit 88, and a treatment effect determination unit 89. Although each of the component members 51 through 54b, 60E and 82 through 89 shown in FIGS. 27 and 28 is described as functions of the CPU 35E, the present invention is not limited thereto. Each of the component members 51 through 54b, 60E and 82 through 89 may be a hardware device included in the medical image processing apparatus 70E.

In the medical image processing system 1E according to the sixth embodiment shown in FIGS. 27 and 28, functions identical to those of the medical image processing system 1 according to the first embodiment shown in FIGS. 2 and 3 are designated by identical reference numerals to omit a description thereof.

Referring to FIG. 27, the first angiographic image acquisition unit 51 has a function to acquire angiographic images that are pre-treatment data.

The third angiographic image acquisition unit 82 has a function to acquire post-treatment data that is data on angiographic images (including non-contrast enhanced MRA images obtained without a contrast agent) collected by medical diagnostic imaging apparatuses such as X-ray CT apparatuses, MRI apparatuses and contrast-enhanced X-ray image diagnostic apparatuses via a storage device such as the HDD 37 or the network N, and the communication controller 39.

The third volume data generation unit 83 has a function to three-dimensionally reconstruct an angiographic image acquired by the third angiographic image acquisition unit 82 and to generate volume data for three-dimensional image processing.

The third cerebral blood vessel extraction unit 84 has a function to extract cerebral blood vessel data from the volume data generated by the third volume data generation unit 83.

The third collateral circulation extraction unit 85 has a function to extract collateral circulations from the entire cerebral blood vessels extracted by the third cerebral blood vessel extraction unit 84. The third collateral circulation extraction unit 85 extracts a collateral circulation as a region having a highest existence probability based on comparison with Atlas, estimation with feature values, or estimation with a morphological filter.

Referring to FIG. 28, the third ischemic blood vessel extraction unit 86 has a function to extract ischemic blood vessels, based on the entire cerebral blood vessels extracted by the third cerebral blood vessel extraction unit 84 shown in FIG. 27 and the collateral circulations extracted by the third collateral circulation extraction unit 85 shown in FIG. 27.

The collateral circulation evaluation unit 87 has a function to evaluate a level of recovery by treatment, based on the collateral circulations extracted by the first collateral circulation extraction unit 54a shown in FIG. 27 and the collateral circulations extracted by the third collateral circulation extraction unit 85 shown in FIG. 27. The collateral circulation evaluation unit 87 calculates, for example, a time-series volume shrinkage rate of a collateral circulation and evaluates (quantifies) the level of recovery by treatment as compared with a general tendency when the same treatment is performed.

The ischemic blood vessel evaluation unit 88 has a function to evaluate the level of recovery by treatment, based on the ischemic blood vessels extracted by the first ischemic blood vessel extraction unit 54b shown in FIG. 27 and the ischemic blood vessels extracted by the third ischemic blood vessel extraction unit 86. The ischemic blood vessel evaluation unit 88 calculates, for example, a time-series volume expansion rate of an ischemic blood vessel and evaluates (quantifies) the level of recovery by treatment.

The treatment effect determination unit 89 has a function to determine whether or not a recovery speed of moyamoya disease is favorable based on the volume shrinkage rate of the collateral circulation by the collateral circulation evaluation unit 87 and the volume expansion rate of the ischemic blood vessel by the ischemic blood vessel evaluation unit 88 so as to determine a treatment effect against moyamoya disease.

The image synthesis unit 60E has a function to synthesize the collateral circulations extracted by the first collateral circulation extraction unit 54a shown in FIG. 27, the ischemic blood vessels extracted by the first ischemic blood vessel extraction unit 54b shown in FIG. 27, the collateral circulations extracted by the third collateral circulation extraction unit 85 shown in FIG. 27, and the ischemic blood vessels extracted by the third ischemic blood vessel extraction unit 86, to provide a setting so that each blood vessel has an independent display attribute, to perform rendering, and to further synthesize a treatment result determined by the treatment effect determination unit 89 to generate synthesized image data. The synthesized image also includes synthesized text information and scales of various parameters or the like. The synthesized image generated by the image synthesis unit 60E is sent to the display device 34 as video signals and is displayed through the display device 34.

Figure 29:
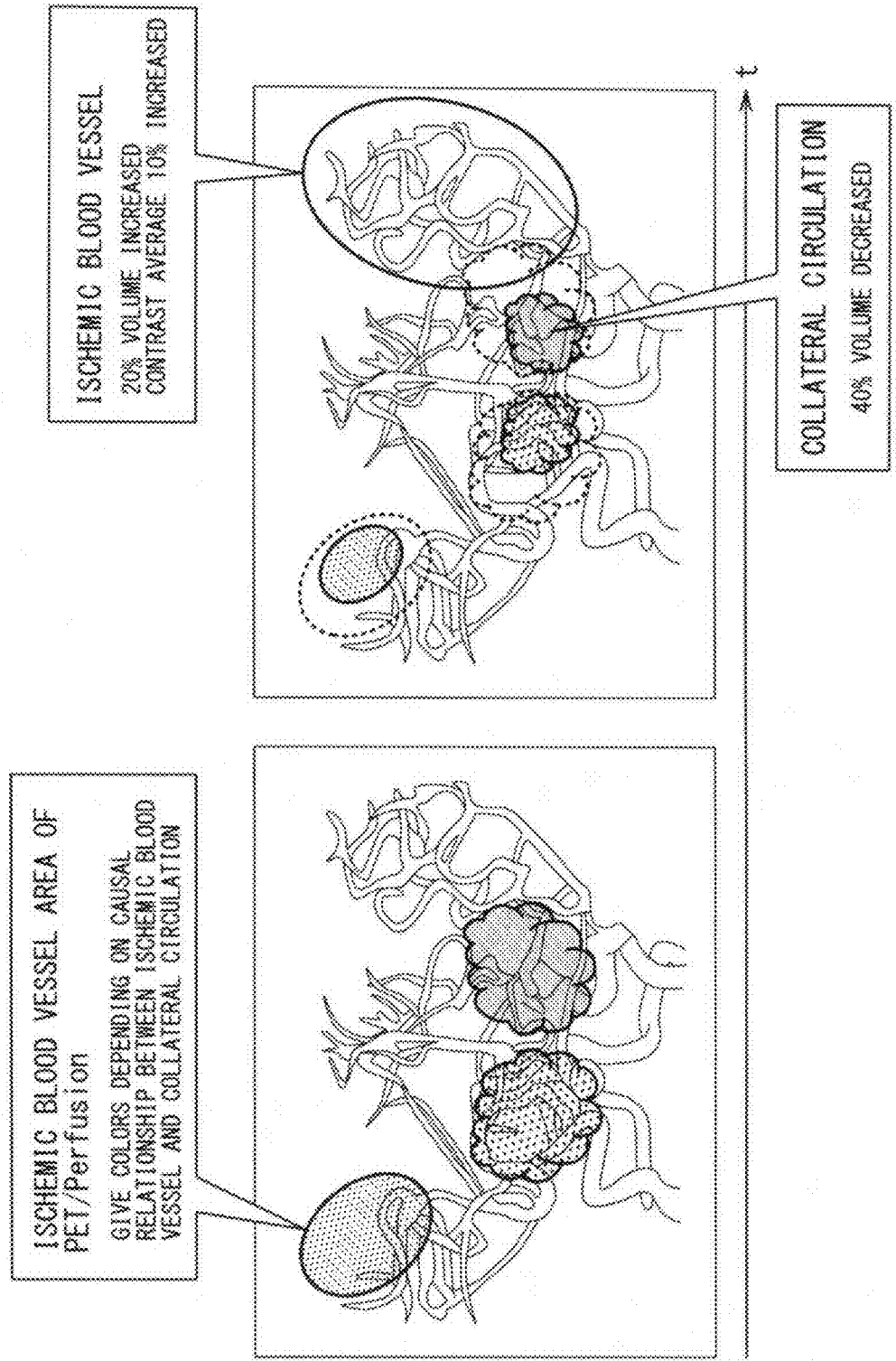
FIG. 29 is a diagram showing an example of a determined treatment result to be displayed.

FIG. 29 is a diagram showing an example of a determined treatment result to be displayed.

A left-hand side of FIG. 29 shows a synthesized image of pre-treatment collateral circulations and ischemic blood vessels. A right-hand side of FIG. 29 shows a synthesized image of post-treated collateral circulations and ischemic blood vessels, and the determined treatment result. Furthermore, as shown on the right-hand side of FIG. 29, the pre-treated collateral circulations and ischemic blood vessels may be displayed with the post-treated synthesized image by being synthesized therewith.

In the vicinity of a display of the post-treated collateral circulation shown in the right-hand side of FIG. 29, the level of recovery by the treatment evaluated by the collateral circulation evaluation unit 87 is quantitatively displayed ("40% volume decreased"). In the vicinity of a display of the post-treated ischemic blood vessels shown on the right-hand side of FIG. 29, the level of recovery by the treatment evaluated by the ischemic blood vessel evaluation unit 88 is quantitatively displayed ("20% volume increased"), and the level of recovery of ischemia is quantitatively displayed ("contrast average 10% increased").

According to the medical image processing system 1E in the sixth embodiment, cerebral blood vessels in a contrast-enhanced X-ray image are sorted into collateral circulations and ischemic blood vessels, and each vessel is displayed with an independent display attribute, so that vessel structures can be displayed as a visible image.

Seventh Embodiment

Since an object of a seventh embodiment is to perform post-imaging processing of a diagnostic imaging workstation or the like as in the fourth through sixth embodiments, the seventh embodiment does not have functions to collect and process images in real time. The seventh embodiment is applied to, for example, a direct bypass operation (superficial temporal artery-middle cerebral artery anastomosis) against moyamoya disease. The direct bypass operation is an anastomosis operation between an arteria cerebri media traveling on a cerebral surface and a superficial temporal artery that mainly supplies nutrition to skins and subcutaneous tissues of a head.

Figure 30:
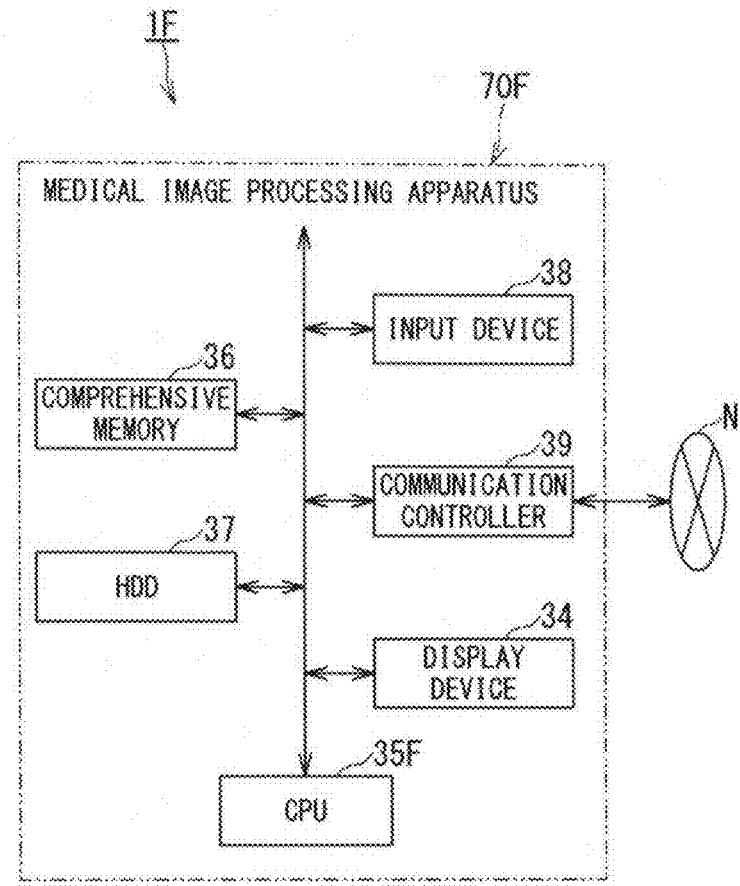
FIG. 30 is a schematic diagram showing an example of a structure of a medical image processing system according to a seventh embodiment.

FIG. 30 is a schematic diagram showing one example of a structure of a medical image processing system according to the seventh embodiment.

FIG. 30 shows a medical image processing system 1F according to the seventh embodiment. The medical image processing system 1F includes a medical image processing apparatus 70F. The medical image processing apparatus 70F, which is structured by a computer as a base, can mutually communicate with a network N. The medical image processing apparatus 70F is mainly constituted of basic hardware devices such as a display device 34, a CPU 35F, a comprehensive memory 36, an HDD 37, an input device 38, and a communication controller 39. The CPU 35F is mutually connected with respective hardware components that constitute the medical image processing apparatus 70F via a bus as a common signal transmission line. The medical image processing apparatus 70F may include a storage medium drive (not shown).

In the medical image processing system 1F according to the seventh embodiment shown in FIG. 30, component members identical to those of the medical image processing system 1 according to the first embodiment shown in FIG. 1 are designated by identical reference numerals to omit a description thereof.

Figure 31:
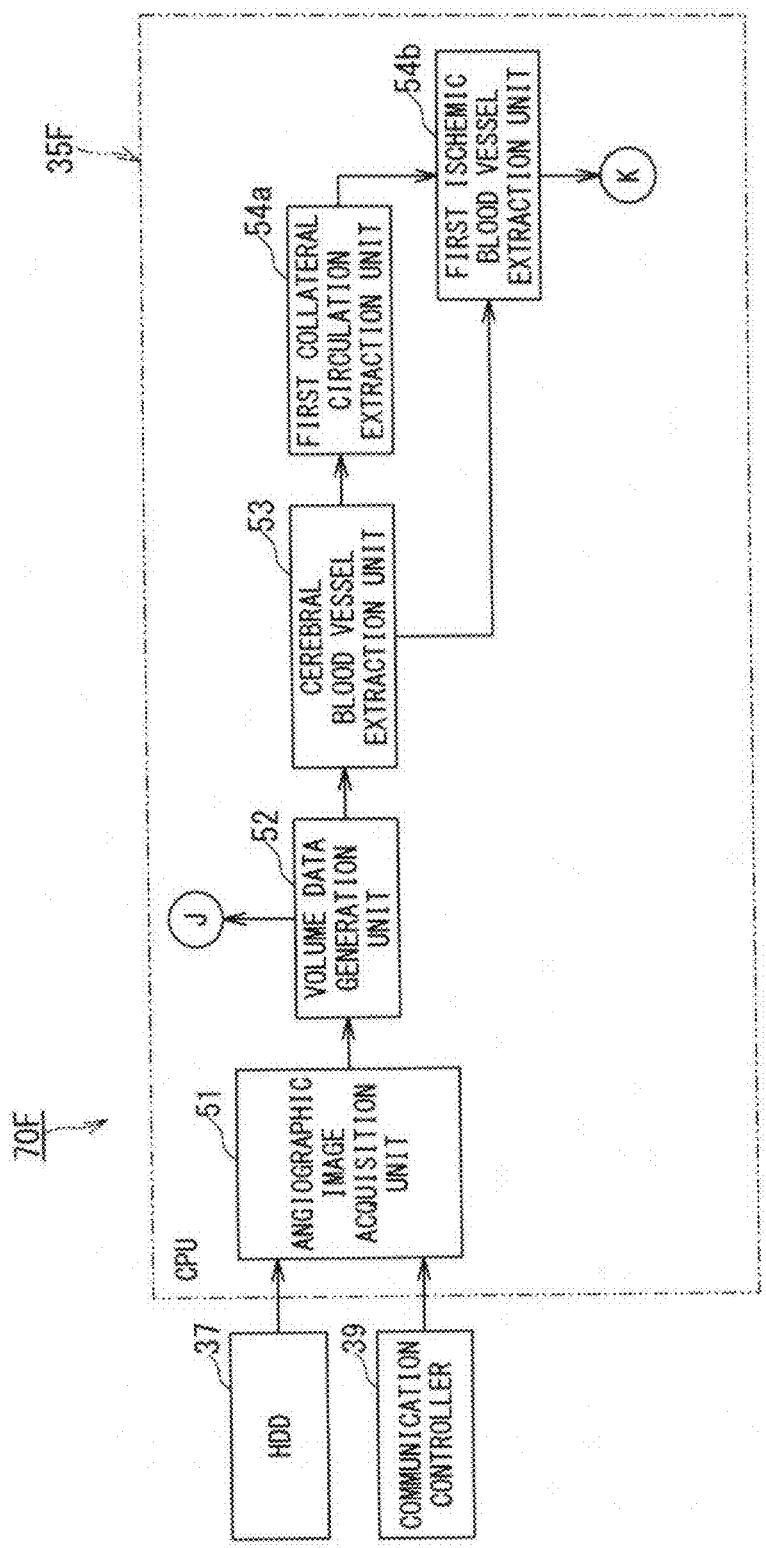
FIG. 31 is a block diagram showing functions of a medical image processing apparatus in the medical image processing system according to the seventh embodiment.
Figure 32:
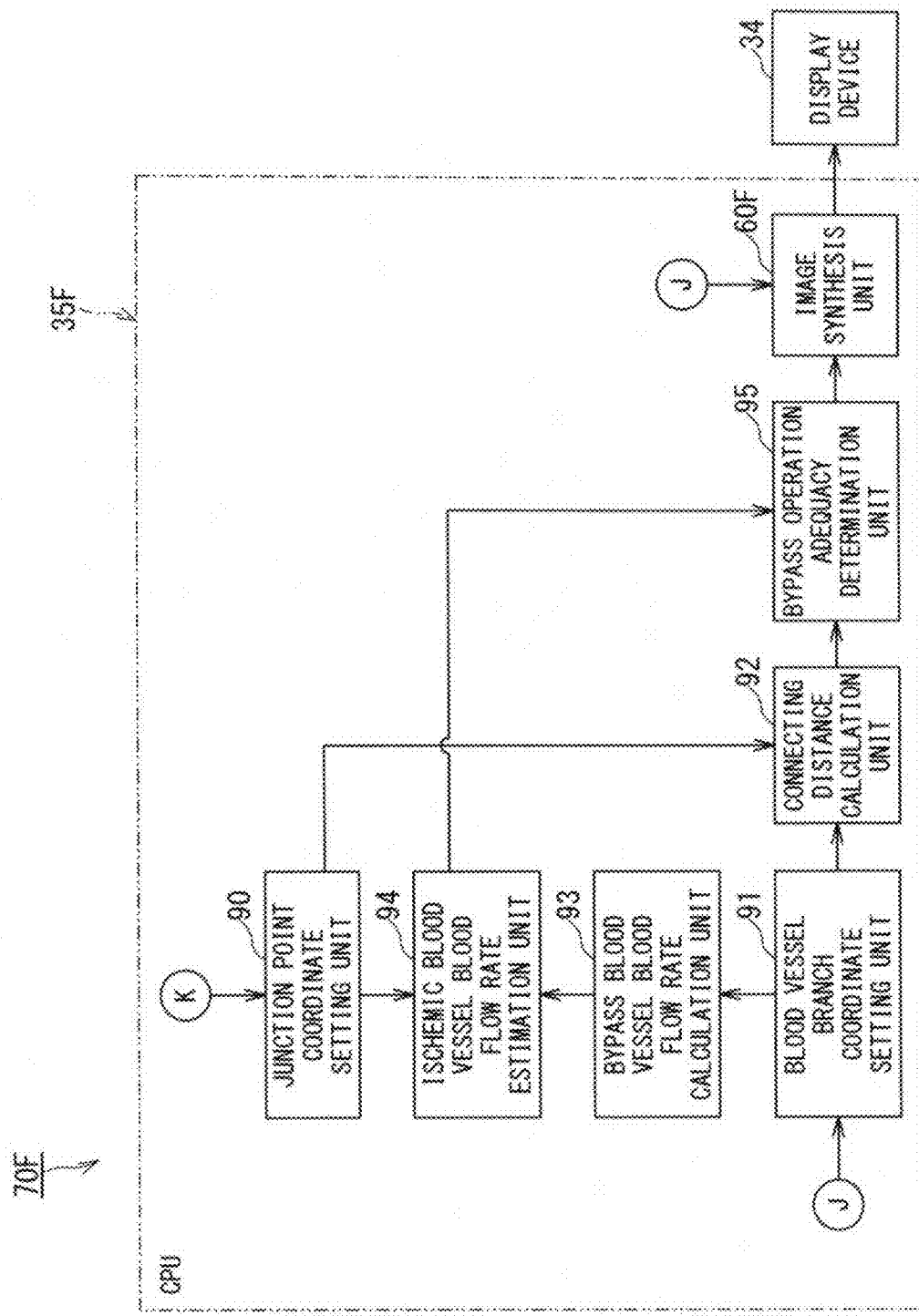
FIG. 32 is a block diagram showing functions of the medical image processing apparatus in the medical image processing system according to the seventh embodiment.

FIGS. 31 and 32 are block diagrams showing functions of the medical image processing apparatus 70F in the medical image processing system 1F according to the seventh embodiment.

When the CPU 35F shown in FIG. 30 executes a program, the medical image processing apparatus 70F functions, as shown in FIGS. 31 and 32, as an angiographic image acquisition unit 51, a volume data generation unit 52, a cerebral blood vessel extraction unit 53, a first collateral circulation extraction unit 54a, a first ischemic blood vessel extraction unit 54b, an image synthesis unit 60F, a junction point coordinate setting unit 90, a blood vessel branch coordinate setting unit 91, a connecting distance calculation unit 92, a bypass blood vessel blood flow rate calculation unit 93, an ischemic blood vessel blood flow rate estimation unit 94, and a bypass operation adequacy determination unit 95. Although each of the component members 51 through 54b, 60F and 90 through 95 shown in FIGS. 31 and 32 is described as functions of the CPU 35F, the present invention is not limited thereto. Each of the component members 51 through 54b, 60F and 90 through 95 may be a hardware device included in the medical image processing apparatus 70F.

In the medical image processing system 1F according to the seventh embodiment shown in FIGS. 31 and 32, functions identical to those of the medical image processing system 1 according to the first embodiment shown in FIGS. 2 and 3 are designated by identical reference numerals to omit a description thereof.

Referring to FIG. 32, the junction point coordinate setting unit 90 has a function to set a bypass position as a junction point coordinate (three-dimensional coordinate system) on an arteria cerebri media regarded as an ischemic blood vessel extracted by the first ischemic blood vessel extraction unit 54b shown in FIG. 31. For example, the junction point coordinate setting unit 90 sets a junction point coordinate on the arteria cerebri media based on the junction point coordinate selected by an operator with use of the input device 38.

The blood vessel branch coordinate setting unit 91 has a function to set a bypass blood vessel branch as a blood vessel branch coordinate (three-dimensional coordinate system) on a superficial temporal artery, based on volume data generated by the volume data generation unit 52 shown in FIG. 31. For example, the blood vessel branch coordinate setting unit 91 sets a blood vessel branch coordinate on a superficial temporal artery based on the blood vessel branch coordinate selected by the operator with use of the input device 38.

The connecting distance calculation unit 92 has a function to calculate a distance required for connection between a junction point coordinate and a blood vessel branch coordinate based on the junction point coordinate set by the junction point coordinate setting unit 90 and the blood vessel branch coordinate set by the blood vessel branch coordinate setting unit 91.

The bypass blood vessel blood flow rate calculation unit 93 has a function to calculate a blood flow rate of a bypass superficial temporal artery before bypass treatment, based on the blood vessel branch coordinate set by the blood vessel branch coordinate setting unit 91. The blood flow rate calculated by the bypass blood vessel blood flow rate calculation unit 93 is calculated based on time-series changes in a signal value of a cerebral blood vessel on a taken image.

The ischemic blood vessel blood flow rate estimation unit 94 has a function to estimate a blood flow rate of the arteria cerebri media that is regarded as an ischemic blood vessel before bypass treatment, based on the blood flow rate of the bypass superficial temporal artery calculated by the bypass blood vessel blood flow rate calculation unit 93 and the junction point coordinate set by the junction point coordinate setting unit 90.

The bypass operation adequacy determination unit 95 has a function to estimate a blood flow rate of the arteria cerebri media after bypass treatment, based on a blood flow rate of the arteria cerebri media regarded as an ischemic blood vessel before bypass treatment, the blood flow rate being estimated by the ischemic blood vessel blood flow rate estimation unit 94 and based on a connecting distance calculated by the connecting distance calculation unit 92, and to simulate whether or not ischemia can sufficiently be ameliorated. The bypass operation adequacy determination unit 95 determines, based on threshold processing or the like, whether or not a selected bypass superficial temporal artery is adequate for treatment.

The image synthesis unit 60F has a function to synthesize a rendering image of the volume data generated by the volume data generation unit 52 shown in FIG. 31 and a result of determination regarding adequacy of the direct bypass operation made by the bypass operation adequacy determination unit 95 to generate synthesized image data. The synthesized image also includes synthesized text information and scales of various parameters or the like. The synthesized image generated by the image synthesis unit 60F is sent to the display device 34 as video signals and is displayed through the display device 34.

According to the medical image processing system 1F in the seventh embodiment, cerebral blood vessels in a contrast-enhanced X-ray image are sorted into collateral circulations and ischemic blood vessels, and each vessel is displayed with an independent display attribute, so that vessel structures can be displayed as a visible image.

Also according to the medical image processing system 1F in the seventh embodiment, cerebral blood vessels in a contrast-enhanced X-ray image are sorted into collateral circulations and ischemic blood vessels, so that adequacy evaluation of the direct bypass operation can accurately be performed.

In the first to seventh embodiments, the brain of the patient P has been described as a target region for easy understanding. However, it should naturally be understood that the present invention is not limited to the example where the brain of the patient P is a target region.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical image processing system, comprising:
a memory configured to store an angiographic image of a region including a blood vessel; and
a processing circuit configured to
acquire the angiographic image from the memory;
three-dimensionally reconstruct the angiographic image to generate volume data;
extract blood vessels on the basis of the volume data;
sort the blood vessels into at least a collateral circulation and an ischemic blood vessel;
apply different filtering processes to the collateral circulation and the ischemic blood vessel; and
generate a synthesized image.

2. The medical image processing system according to claim 1, wherein the processing circuit is further configured to acquire a function image on a region including the blood vessel; and
apply different image processes to the collateral circulation, the ischemic blood vessel, and the function image; and
generate the synthesized image.

3. The medical image processing system according to claim 1, wherein the processing circuit is further configured to
acquire the angiographic image, a pre-treated angiographic image, and a post-treated angiographic image;
generate pre-treatment volume data based on the pre-treatment angiographic image and post-treatment volume data based on the post-treatment angiographic image;
extract pre-treated blood vessels based on the pre-treatment volume data and post-treated blood vessels based on the post-treatment volume data;
sort the pre-treated blood vessels into at least a pre-treated collateral circulation and a pre-treated ischemic blood vessel and sort the post-treated blood vessels into at least a post-treated collateral circulation and a post-treated ischemic blood vessel;
calculate a volume shrinkage rate of a collateral circulation on the basis of the pre-treated collateral circulation and the post-treated collateral circulation;
calculate a volume expansion rate of an ischemic blood vessel on the basis of the pre-treated ischemic blood vessel and the post-treated ischemic blood vessel; and determine a treatment effect on the basis of the volume shrinkage rate of the collateral circulation and the volume expansion rate of the ischemic blood vessel.

4. The medical image processing system according to claim 1, wherein the processing circuit is further configured to set, as a junction point coordinate, a bypass position on an arteria cerebri media regarded as the ischemic blood vessel;

set, as a blood vessel branch coordinate, a bypass blood vessel branch on a superficial temporal artery on the basis of the volume data;

calculate a distance required for connection between the junction point coordinate and the blood vessel branch coordinate on the basis of the junction point coordinate and the blood vessel branch coordinate;

calculate a blood flow rate of a bypass superficial temporal artery before bypass treatment on the basis of the blood vessel branch coordinate;

estimate a blood flow rate of the arteria cerebri media before bypass treatment on the basis of the blood flow rate of the bypass superficial temporal artery and the junction point coordinate; and estimate a blood flow rate of the arteria cerebri media after bypass treatment on the basis of the blood flow rate of the arteria cerebri media before bypass treatment and of the connecting distance, and to determine whether or not the bypass superficial temporal artery is adequate for treatment.

5. The medical image processing system according to claim 1, wherein the processing circuit is further configured to apply suppression filtering to the collateral circulation in the contrast-enhanced X-ray image, while applying highlight filtering to the ischemic blood vessel in the imaging X-ray image.

6. A medical image processing system, comprising:

a memory configured to store an angiographic image of a region including a blood vessel; and a processing circuit configured to acquire the angiographic image from the memory;

three-dimensionally reconstruct the angiographic image to generate volume data;

extract blood vessels on the basis of the volume data;

sort the blood vessels into a collateral circulation and an ischemic blood vessel;

acquire a contrast-enhanced X-ray image based on an angiography imaging;

align the volume data and the contrast-enhanced X-ray image;

sort blood vessels of the contrast-enhanced X-ray image into at least a collateral circulation and an ischemic blood vessel on the basis of the collateral circulation and the ischemic blood vessel in the volume data;

different filtering processes to the collateral circulation and the ischemic blood vessel in the contrast-enhanced X-ray image; and generate a synthesized image.

7. The medical image processing system according to claim 6, wherein the processing circuit is configured to apply suppression filtering to the collateral circulation in the contrast-enhanced X-ray image, while applying highlight filtering to the ischemic blood vessel in the imaging X-ray image.

8. The medical image processing system according to claim 6, wherein the processing circuit is configured to generate a raysum fluoroscopic image on the basis of the volume data, and to align the raysum fluoroscopic image and the contrast-enhanced X-ray image.

9. The medical image processing system according to claim 6, wherein the processing circuit is further configured to extract the collateral circulation on the basis of the blood vessel in the volume data;

extract the ischemic blood vessel from the volume data on the basis of the blood vessel and the collateral circulation;

extract a normal blood vessel from the volume data on the basis of the blood vessel, the collateral circulation, and the ischemic blood vessel, sort, on the basis of the collateral circulation, the ischemic blood vessel, and the normal blood vessel of the volume data, the blood vessel of the contrast-enhanced X-ray image into the collateral circulation, the ischemic blood vessel, and a normal blood vessel;

apply different image processes to the normal blood vessel in the contrast-enhanced X-ray image, and the filtered collateral circulation, and the ischemic blood vessel; and generate the synthesized image.

10. The medical image processing system according to claim 6, wherein the processing circuit is further configured to synthesize a rendering image of the volume data, the filtered collateral circulation, and the ischemic blood vessel.

11. The medical image processing system according to claim 6, wherein the processing circuit is further configured to detect a tip position of a treatment catheter;

determine whether or not the treatment catheter tip position has entered into the collateral circulation; and issue, when the processing circuit determines that the treatment catheter tip position has entered into the collateral circulation, an alarm.

12. The medical image processing system according to claim 6, further comprising:

an X-ray image diagnostic apparatus configured to collect X-ray images; and a contrast agent injector connected to a contrast agent catheter, and configured to inject a contrast agent into the contrast agent catheter, wherein the contrast-enhanced X-ray image is generated by the X-ray image diagnostic apparatus and the contrast agent injector.

13. The medical image processing system according to claim 6, wherein the processing circuit is further configured to apply different image processes to the filtered collateral circulation and the ischemic blood vessel.

* * * * *